US008008543B2

(12) United States Patent
Mouradov et al.

(10) Patent No.: US 8,008,543 B2
(45) Date of Patent: Aug. 30, 2011

(54) MODIFICATION OF FLAVONOID BIOSYNTHESIS IN PLANTS BY PAP1

(75) Inventors: Aidyn Mouradov, Mill Park (AU); German Spangenberg, Bundoora (AU)

(73) Assignee: Agriculture Victoria Services PTY Ltd, Attwood, Victoria (AU)

( * ) Notice: Subject to any disclaimer, the term of this patent is extended or adjusted under 35 U.S.C. 154(b) by 519 days.

(21) Appl. No.: 12/091,546

(22) PCT Filed: Oct. 25, 2006

(86) PCT No.: PCT/AU2006/001590
§ 371 (c)(1),
(2), (4) Date: Apr. 25, 2008

(87) PCT Pub. No.: WO2007/048189
PCT Pub. Date: May 3, 2007

(65) Prior Publication Data
US 2009/0113573 A1 Apr. 30, 2009

(30) Foreign Application Priority Data

Oct. 26, 2005 (AU) ................................ 2005905942

(51) Int. Cl.
*A01H 1/00* (2006.01)
*A01H 5/00* (2006.01)
*C12N 5/14* (2006.01)
*C12N 15/05* (2006.01)
*C07H 21/04* (2006.01)
*C07K 14/415* (2006.01)

(52) U.S. Cl. .................... 800/278; 536/23.6; 435/320.1; 530/350

(58) Field of Classification Search ........................ None
See application file for complete search history.

(56) References Cited

U.S. PATENT DOCUMENTS

| | | | |
|---|---|---|---|
| 6,573,432 B1 | 6/2003 | Borevitz et al. | |
| 2004/0031072 A1* | 2/2004 | La Rosa et al. | 800/278 |
| 2004/0034888 A1 | 2/2004 | Liu et al. | |
| 2004/0045049 A1 | 3/2004 | Zhang et al. | |
| 2004/0123339 A1 | 6/2004 | Conner et al. | |
| 2009/0083874 A1* | 3/2009 | Dixon et al. | 800/260 |

FOREIGN PATENT DOCUMENTS

| | | |
|---|---|---|
| JP | 2005204657 A | 8/2005 |
| WO | 0132002 A1 | 5/2001 |
| WO | 0200902 A2 | 1/2002 |
| WO | 02055658 A2 | 7/2002 |
| WO | 2004002215 A2 | 1/2004 |
| WO | 2006010096 A2 | 1/2006 |

OTHER PUBLICATIONS

Borevitz, et al., "Activation tagging identifies a conserved MYB regulator of phenylpropanoid biosynthesis.", The Plant Cell, 2000, pp. 2383-2393, vol. 12.

Padmanabhan, et al., "Interaction of the Tobacco Mosaic Virus Replicase Protein with the Aux/IAA Protein PAP1/ IAA26 Is Associated with Disease Development", Journal of Virology, Feb. 2005, pp. 2549-2558; vol. 79, No. 4.
Sharma, et al, "Metabolic engineering of proanthocyanidins by ectopic expression of transcription factors in *Arabidopsis thaliana*", The Plant Journal, 2005, pp. 62-75; vol. 44.
Teng, et al, "Sucrose-Specific Induction of Anthocyanin Biosynthesis in *Arabidopsis* Requires the MYB75/PAP1 Genet ", Plant Physiology, Dec. 2005, pp. 1840-1852, vol. 139.
Tohge, et al., "Enhanced radical scavenging activity of genetically modified *Arabidopsis* seeds", Biotechnology Letters, 2005, pp. 297-303; vol. 27.
Xie, et al., "Metabolic engineering of proanthocyanidins through co-expression of anthocyanidin reductase and the PAP1 MYB transcription factor", The Plant Journal, 2006, pp. 895-907, vol. 45.
Kobayashi, et al., Genbank Accession No. AB073010, "*Vitis labrusca x Vitis vinifera* VlmybA1-1 gene for myb-related transcription factor V1MYBA1-1, complete cds.", Aug. 16, 2002.
Kobayashi, et al., Genbank Accession No. AB073012, "*Vitis labrusca x Vitis vinifera* VlmybA1-2 gene for myb-related transcription factor V1MYBA1-2, complete cds.", Aug. 16, 2002.
Kobayashi, et al., Genbank Accession No. AB073013, "*Vitis labrusca x Vitis vinifera* VlmybA2 gene for myb-related transcription factor V1MYBA2, complete cds", Aug. 16, 2002.
Kobayashi, et al., Genbank Accession No. AB097923, "*Vitis vinifera* VvmybA1 mRNA for myb-related transcription factor VvMYBA1, complete cds.", May 15, 2004.
Kobayashi, et al., Genbank Accession No. AB097924, "*Vitis vinifera* VvmybA2 mRNA for myb-related transcription factor VvMYBA2, complete cds.", May 15, 2004.
Kobayashi, et al., Genbank Accession No. AB097925, "*Vitis vinifera* VvmybA3 mRNA for myb-related transcription factor VvMYBA3, complete cds.", May 15, 2004.
Quattrocchio, et al., Genbank Accession No. AF146707, "Petunia x hybrida An2 truncated protein (an2) mRNA, an2-W44 allele, complete cds.", May 1, 2000.
Borevitz, et al., Genbank Accession No. AF325123, "*Arabidopsis thaliana* production of anthocyanin pigment 1 protein (PAP1) gene, complete cds.", Dec. 21, 2000.
Borevitz, et al., Genbank Accession No. AF325124, "*Arabidopsis thaliana* production of anthocyanin pigment 2 protein (PAP2) mRNA, complete cds.", Dec. 21, 2000.
Elomaa, et al., Genbank Accession No. AJ554700, "Gerbera hybrid cv. 'Terra Regina' mRNA MYB10 protein.", Apr. 15, 2005.
Mathews, et al., Genbank Accession No. AY348870, "*Lycopersicon esculentum* anthocyanin 1 (ANT1) mRNA, complete cds." Aug. 24, 2003.
Jung, et al., Genbank Accession No. AY841127, "*Solanum tuberosum* cultivar Y83-1 anthocyanin 1 (an1) mRNA, an1-816 allele, complete cds.", Dec. 1, 2005.

(Continued)

Primary Examiner — Eileen B O'Hara
(74) Attorney, Agent, or Firm — Larson & Anderson, LLC

(57) ABSTRACT

The present invention relates to nucleic acids encoding flavonoid biosynthetic enzymes, more particularly flavonoid biosynthesis-regulating transcription factors, and the use thereof for the modification of flavonoid biosynthesis in plants. The present invention also relates to constructs and vectors including such nucleic acids, and related polypeptides. More particularly, the present invention relates to a PURPLE ANTHOCYANIN PIGMENT 1 (PAP1) or PAP1-like transcription factor.

12 Claims, 12 Drawing Sheets

OTHER PUBLICATIONS

Schwinn, et al., Genbank Accession No. DQ275530, "*Antirrhinum majus* ROSEA2 (Rosea2) mRNA, complete cds.", Nov. 26, 2005.

Quattrocchio et al, "Molecular Analysis of the anthocyanin2 Gene of Petunia and Its Role in the Evolution of Flower Color", Oct. 1, 2000, XP002516695 retrieved from EBI accession No. UNIPROT:Q9M721.

Dixon et al., "Proanthocyanidins—a final frontier in flavonoid research?", The New Phytologist, Jan. 2005, pp. 9-28, vol. 165, No. 1, XP002516051.

Elomaa et al., "Activation of Anthocyanin Biosynthesis in Gerbera hybrida (*Asteraceae*) Suggests Conserved Protein-Protein and Protein-Promoter Interactions between the Anciently Diverged Monocots and Eudicots1", Plant Physiology, Dec. 1, 2003, pp. 1831-1842, vol. 133, XP002517075 database accession No. AJ554700.

Kobayashi et al., "Myb-related genes of the Kyoho grape (*Vitis labruscana*) regulate anthocyanin biosynthesis", Planta, Oct. 1, 2002, pp. 924-933, vol. 215, Springer-Verlag, DE, XP002966677.

Kobayashi et al., "Retrotransposon-Induced Mutations in Grape Skin Color", Science (Washington, DC), May 14, 2004, p. 982, vol. 304, XP002517072.

Tohge et al., "Functional genomics by integrated analysis of metabolome and transcriptome of *Arabidopsis* plants over-expressing an MYB transcription factor", The Plant Journal, Apr. 2005, pp. 218-235, vol. 42, No. 2, Blackwell Publishing Ltd, GB, XP002516050.

Quattrocchio et al., "Molecular Analysis of the anthocyanin2 Gene of Petunia and Its Role in the Evolution of Flower Color", The Plant Cell, Aug. 1999, pp. 1433-1444, vol. 11., American Society of Plant Physiologists, XP002517071, database accession No. AF146704.

Kobayashi et al., "Myb-related genes of the Kyoho grape (*Vitis labruscana*) regulate anthocyanin biosynthesis", Oct. 1, 2002, XP002516696 retrieved from EBI accession No. UNIPROT:Q8L5P3.

Quattrocchio et al, "Molecular Analysis of the anthocyanin2 Gene of Petunia and Its Role in the Evolution of Flower Color", May 1, 2000, XP002517073 accession No. EM_PL:AF146704.

Elomaa et al., "Activation of Anthocyanin Biosynthesis in Gerbera hybrida (*Asteraceae*) Suggests Conserved Protein-Protein and Protein-Promoter Interactions between the Anciently Diverged Monocots and Eudicots1", Jan. 5, 2004, XP002517075 accession No. EM_PL:AJ554700.

Borovsky et al, "The A locus the controls anthocyanin accumulation in pepper encodes a MYB transcription factor homologous to Anthocyanin2 of Petunia", Mar. 26, 2004, XP002517074 accession No. EM_PL:AJ608992.

Mathews et al., "Activation tagging in tomato identifies a transcriptional regulator of anthocyanin biosynthesis, modification, and transport", Aug. 28, 2003, XP002517076 accession No. EM_PL:AY348870.

Kobayashi et al., "Retrotransposon-Induced Mutations in Grape Skin Color", Jul. 5, 2004, XP002516697 retrieved from EBI accession No. UNIPROT:Q6L973.

Mathews et al., "Activation tagging in tomato identifies a transcriptional regulator of anthocyanin biosynthesis, modification, and transport", Jul. 5, 2004, XP002516694 retrieved from EBI accession No. UNIPROT:Q6V7V0.

Elomaa et al., "Activation of Anthocyanin Biosynthesis in Gerbera hybrida (*Asteraceae*) Suggests Conserved Protein-Protein and Protein-Promoter Interactions between the Anciently Diverged Monocots and Eudicots1", Jul. 5, 2004, XP002516693 retrieved from EBI accession No. UNIPROT:Q7ORD0.

Borovsky et al., "The A locus the controls anthocyanin accumulation in pepper encodes a MYB transcription factor homoogous to Anthocyanin2 of Petunia", Jul. 5, 2004, XP002516692 retrieved from EBI accession No. UNIPROT:Q708Y2.

Altschul, Stephen et al. "Basic Local Alignment Search Tool", 1990, pp. 403-410, vol. 215, J. Mol. Biol.

Frohman, Michael et al. "Rapid production of full-length cDNAs from Rare Transcripts: Amplification using a single gene-specfic oligonulceotide primer", Dec. 1988, pp. 8998-9002, vol. 85, PNAS.

Gish, William et al. "Identification of protein coding regions by database similarity search", Mar. 1993, pp. 266-272, vol. 3, Nature Publishing Group.

Goderis, Inge et al. "A set of modular plant transformation vectors allowing flexible insertion of up to six expression units", 2002, pp. 17-27, vol. 50, Plant Molecular Biology.

Hajdukiewicz, Peter et al. "The small, versatile pPZP family of Agrobacterium binary vectors for plant transformation", 1994, pp. 989-994, vol. 25, Plant Molecular Biology.

Loh, Elwyn et al. "Polymerase Chain Reaction with Single-Sided Specificity: Analysis of T Cell Receptor σ Chain", 1989, pp. 217-220, vol. 243, No. 4888, Science AAAS.

Ohara, Osamu et al. "One-Sided polymerase chain reaction: The amplification of cDNA", 1989, pp. 5673-5677, vol. 86, PNAS.

Paolocci, Francesco et al. "Light and an exogenous transcription factor qualitatively and quantitatively affect the biosynthetic pathway of condensed tannins in *Lotus corniculatus* leaves", Apr. 2005, pp. 1093-1103, vol. 56, No. 414, Journal of Experimental Botany.

Xie, De-Yu et al. "Role of Anthocyanidin Reductase, Encoded by BANYULS in Plant Flavonoid Biosynthesis," 2003, pp. 396-399, vol. 299, No. 5605, ProQuest Biology Journal.

* cited by examiner

```
                    *        20         *        40         *        60
TrPAP1 : ATAACACAATATTATATATAAAAGAAGATGCTGGTGATGGCTTGATTATTATGAGTGTGA :  60

*        80         *       100         *       120
TrPAP1 : AAAGTGGTGGTGTTTGTAGAGTCTCATAAGATGGGTGGTGTTGCATGGACAGAAGAAGAA : 120

*       140         *       160         *       180
TrPAP1 : GATCATTTGCTTAAGAAATGCATACAACAATATGGTGAAGGAAAGTGGCATCGAGTTCCT : 180

*       200         *       220         *       240
TrPAP1 : CTGTTGGCAGGTCTAAACAGATGCCGAAAGAGTTGTAGGCTAAGATGGTTGAACTATCTC : 240

*       260         *       280         *       300
TrPAP1 : CGTCCTAACATCAAGAGAGGAAATTTTGCTGAGGAGGAAGTTGAAATGATTGTCAAACTA : 300

*       320         *       340         *       360
TrPAP1 : CACAAATTATTAGGCAACAGATGGTCCCTAATTGCAGGAAGGCTACCAGGAAGGACAGCA : 360

*       380         *       400         *       420
TrPAP1 : AATGATGTGAAAAACTATTGGAATTGTCATCTAAGCAAAAGAGTAAATGCTCTAGAAGCT : 420

*       440         *       460         *       480
TrPAP1 : GACCAAGATGGATCACAATTATCCAAAGATGTTCAAATCATTATGCCACAGCCAAGAAAC : 480

*       500         *       520         *       540
TrPAP1 : AATGGTTCAAGCTCAACAATGAAGAGAAGGAGCCAAGGAGACTCACCAACTAATCAAGTT : 540

*       560         *       580
TrPAP1 : CTAGTTGAACAAGAGAGTGACATGACAAAATTTGATGCTGATG : 583
```

Figure 1

```
              *        20         *        40         *        60
TrPAP1 : MGGVAWTEEEDHLLKKCIQQYGEGKWHRVPLLAGLNRCRKSCRLRWLNYLRPNIKRGNFA :  60

*        80         *       100         *       120
TrPAP1 : EEEVEMIVKLHKLLGNRWSLIAGRLPGRTANDVKNYWNCHLSKRVNALEADQDGSQLSKD : 120

*       140         *       160
TrPAP1 : VQIIMPQPRNNGSSSTMKRRSQGDSPTNQVLVEQESDMTKFDAD : 164
```

Figure 2

```
           *        20         *        40         *        60
: AATTCGATTAAGCAGTGGTAACAACGCAGAGTACGCGGGGACATCTTCAAGAAACATGTG :    60

*        80         *       100         *       120
: TGTGTGTCAATTCACATAACACAATATTATATATAAAAGAAGATGCTGGTGATGGCTTGA :   120

*       140         *       160         *       180
: TTATTATGAGTGTGAAAAGTGGTGGTGTTTGTAGAGTCTCATAAGATGGGTGGTGTTGCA :   180

*       200         *       220         *       240
: TGGACAGAAGAAGAAGATCATTTGCTTAAGAAATGCATACAACAATATGGTGAAGGAAAG :   240

*       260         *       280         *       300
: TGGCATCGAGTTCCTCTGTTGGCAGGTCTAAACAGATGCCGAAAGAGTTGTAGGCTAAGA :   300

*       320         *       340         *       360
: TGGTTGAACTATCTCCGTCCTAACATCAAGAGAGGAAATTTTGCTGAGGAGGAAGTTGAA :   360

*       380         *       400         *       420
: ATGATTGTCAAACTACACAAATTATTAGGCAACAGATGGTCCCTAATTGCAGGAAGGCTA :   420

*       440         *       460         *       480
: CCAGGAAGGACAGCAAATGATGTGAAAAACTATTGGAATTGTCATCTAAGCAAAAGAGTA :   480

*       500         *       520         *       540
: AATGCTCTAGAAGCTGACCAAGATGGATCACAATTATCCAAAGATGTTCAAATCATTATG :   540

*       560         *       580         *       600
: CCACAGCCAAGAAACAATGGTTCAAGCTCAACAATGAAGAGAAGGAGCCAAGGAGACTCA :   600

*       620         *       640         *       660
: CCAACTAATCAAGTTCTAGTTGAACAAGAGAGTGACATGACAAAATTTGATGCTGATGGA :   660

*       680         *       700         *       720
: AAGAACAATATGATTGAATCACAACAAGACATGATGATGTATTCATGCTTAGATCAACAA :   720

*       740         *       760         *       780
: GGTATGTTTAGTGAGTTTCCAATGGACTTTCAATTAGAAGGATTTGAAGCTATGGTAAGT :   780
```

Figure 4A

```
            *        800         *        820         *        840
: GGAGGAGAAGGTAGTAGTAGCCAATGGAATTGGGATGATTTGCTCTTAGATATGGATATG :  840

*        860         *        880         *        900
: TATAATGATTTTTCTTCTTAGATTATCATCCCTTGTTATGTTTCTAATAGGGAAGACAAT :  900

*        920         *        940         *        960
: GGTAGTCTTTATACCTTGGTTGTGTATTAATATCAAAGTTAAATGTTTTCCAAGGAAATG :  960

*        980         *       1000         *       1020
: CATGGTAACTAAATTGGTCATGTATTTTGTAAATTGAAGTCATTGCTAATAAAATTAACC : 1020

*       1040         *       1060         *       1080
: AATAAAGTCGGTCTTGTAAGGCCGAGTTAGTCCAAAAAAAAAAAAAAAAAAAAAAAAAAA : 1080

*       1100         *       1120         *       1140
: AAAAAAAAAAAAAAAAAAAATAAAAAAAAAAAAAAAAAAAAAAAAAAAAAGTACTCTGC : 1140

*       1160
: GTTGTTACCACTGCTTAATCA : 1161
```

Figure 4B

```
            *        20         *        40         *        60
: MGGVAWTEEEDHLLKKCIQQYGEGKWHRVPLLAGLNRCRKSCRLRWLNYLRPNIKRGNFA :  60

*        80         *       100         *       120
: EEEVEMIVKLHKLLGNRWSLIAGRLPGRTANDVKNYWNCHLSKRVNALEADQDGSQLSKD : 120

*       140         *       160         *       180
: VQIIMPQPRNNGSSSTMKRRSQGDSPTNQVLVEQESDMTKFDADGKNNMIESQQDMMMYS : 180

*       200         *       220         *
: CLDQQGMFSEFPMDFQLEGFEAMVSGGEGSSSQWNWDDLLLDMDYNDFSS : 231
```

Figure 5

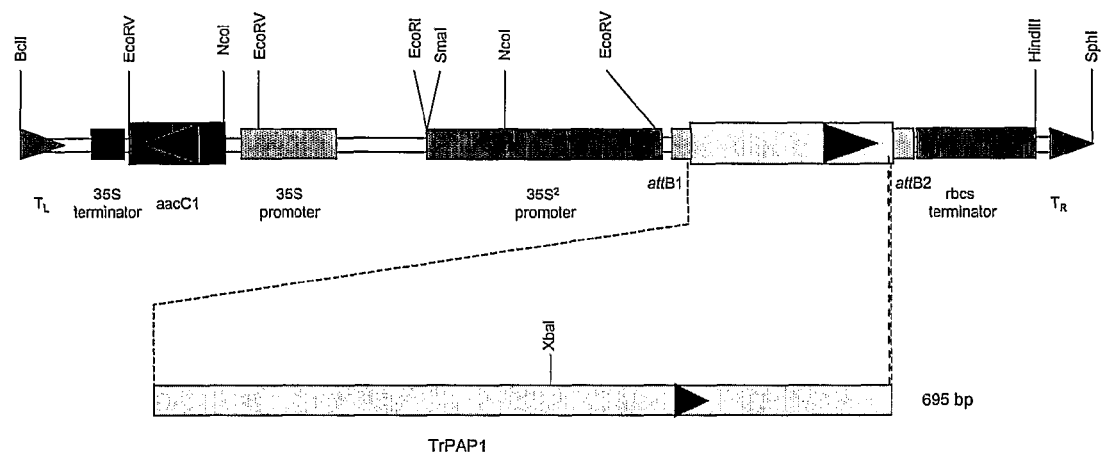
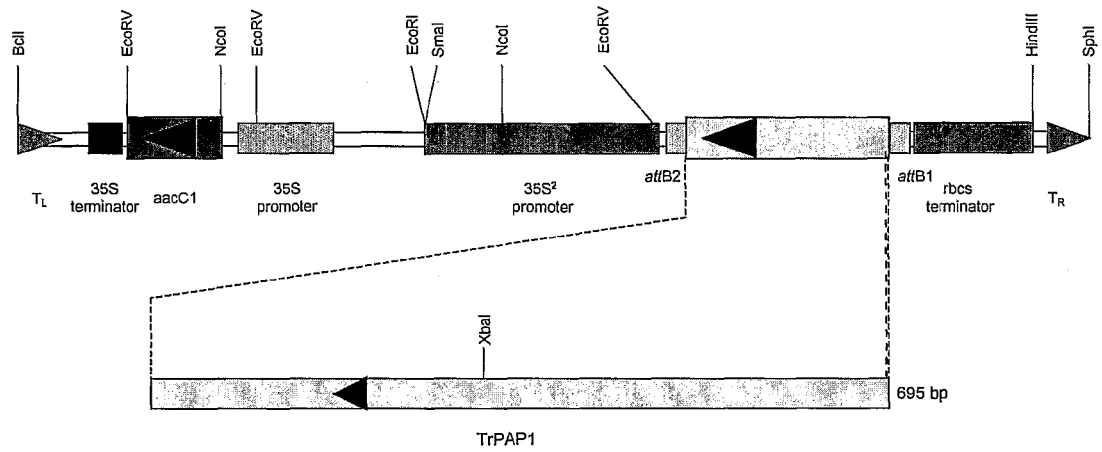
Figure 6

MODIFICATION OF FLAVONOID BIOSYNTHESIS IN PLANTS BY PAP1

The present invention relates generally to nucleic acid fragments and their encoded amino acid sequences for flavonoid biosynthetic enzymes in plants, and the use thereof for the modification of flavonoid biosynthesis in plants.

Flavonoids constitute a relatively diverse family of aromatic molecules that are derived from phenylalanine and malonyl-coenzyme A (CoA, via the fatty acid pathway). These compounds include six major subgroups that are found in most higher plants: the chalcones, flavones, flavonols, flavandiols, anthocyanins and condensed tannins (or proanthocyanidins). A seventh group, the aurones, is widespread, but not ubiquitous.

Some plant species also synthesize specialised forms of flavonoids, such as the isoflavonoids that are found in legumes and a small number of non-legume plants. Similarly, sorghum and maize are among the few species known to synthesize 3-deoxyanthocyanins (or phlobaphenes in the polymerised form). The stilbenes, which are closely related to flavonoids, are synthesised by another group of unrelated species that includes grape, peanut and pine.

Besides providing pigmentation to flowers, fruits, seeds, and leaves, flavonoids also have key roles in signalling between plants and microbes, in male fertility of some species, in defense as antimicrobial agents and feeding deterrants, and in UV protection.

Flavonoids also have significant activities when ingested by animals, and there is great interest in their potential health benefits, particularly for compounds such as isoflavonoids, which have been linked to anticancer benefits, and stilbenes that are believed to contribute to reduced heart disease.

The major branch pathways of flavonoid biosynthesis start with general phenylpropanoid metabolism and lead to the nine major subgroups: the colorless chalcones, aurones, isoflavonoids, flavones, flavonols, flavandiols, anthocyanins, condensed tannins, and phlobaphene pigments. The enzyme phenylalanine ammonia-lyase (PAL) of the general phenylpropanoid pathway will lead to the production of cinnamic acid. Cinnamate-4-hydroxylase (C4H) will produce p-coumaric acid which will be converted through the action of 4-coumaroyl:CoA-ligase (4CL) to the production of 4-coumaroyl-CoA and malonyl-CoA.

In the phenylpropanoid pathway, chalcone synthase (CHS) uses malonyl CoA and 4-coumaryl CoA as substrates. Chalcone reductase (CHR) balances the production of 5-hydroxy- or 5-deoxyflavonoids. The next enzyme, chalcone isomerase (CHI) catalyses ring closure to form a flavanone, but the reaction can also occur spontaneously. Further enzymes in the pathway are: flavanone 3-hydroxylase (F3H), dihydroflavonol 4-reductase (DFR), flavonoid 3'-hydroxylase (F3'H) and flavonoid 3', 5' hydroxylase (F3'5'H).

In the branch of the phenylpropanoid pathway that is specific to condensed tannin and anthocyanin production, leucoanthocyanidins can be reduced to catechins by leucoanthocyanidin reductase (LAR) or to anthocyanidins by leucoanthocyanidin dioxygenase (LDOX). Anthocyanidins can be converted to anthocyanins by the addition of sugar groups, or to epicatechins by anthocyanidin reductase (ANR), encoded by the *BANYULS* gene. Catechins and epicatechins are the subunits of condensed tannins (CTs), which in *Arabidopsis* are thought to be transported into the vacuole by a multidrug secondary transporter-like protein, TRANSPARENT TESTA 12 (TT12), and polymerised by an unknown mechanism.

Enzymes in the flavonoid pathway have been found to be controlled by a range of transcription factors in *Arabidopsis*, maize and petunia. In *Arabidopsis*, condensed tannin biosynthesis requires the function of TRANSPARENT TESTA 2 (TT2), a myb family factor, TRANSPARENT TESTA 8 (TT8), a myc family factor and TRANSPARENT TESTA GLABRA 1 (TTG1), a WD40 family factor, among other transcription factors. These three proteins are thought to form a transcription complex that coordinately activates multiple flavonoid pathway enzymes in order to promote condensed tannin production in *Arabidopsis* seeds. Other myc and myb family transcription factors regulate distinct parts of the flavonoid pathway in maize, petunia and other plant species.

PURPLE ANTHOCYANIN PIGMENT 1 (PAP1) from *Arabidopsis thaliana* belongs to a family of MYB-type transcription factors, including an 2 (*Petunia hybrida*) and ant1 (*Lycopersicon esculentum*), that control anthocyanin production in plants. PAP1 positively regulates the production of anthocyanins in *Arabidopsis* foliage by transcriptionally inducing seven flavonoid pathway enzymes common to flavonoid and condensed tannin biosynthesis, namely, PAL, 4CL, CHS, CHI, F3H, DFR and LDOX.

While nucleic acid sequences encoding PAP1-like transcription factors have been isolated for certain species of plants, there remains a need for materials useful in modifying flavonoid biosynthesis; in modifying protein binding, metal chelation, anti-oxidation, and UV-light absorption; in modifying plant pigment production; in modifying plant defense to biotic stresses such as viruses, microorganisms, insects, fungal pathogens; in modifying forage quality, for example by disrupting protein foam and conferring protection from rumen pasture bloat, particularly in forage legumes and grasses, including alfalfa, medics, clovers, ryegrasses and fescues, and for methods for their use.

It is an object of the present invention to overcome, or at least alleviate, one or more of the difficulties or deficiencies associated with the prior art or to assist in meeting the needs stated above.

In one aspect, the present invention provides substantially purified or isolated nucleic acids or nucleic acid fragments encoding a flavonoid biosynthesis-regulating transcription factor from a legume or grass species. Preferably the nucleic acid or nucleic acid fragment encodes a PAP1 transcription factor, preferably from a clover (*Trifolium*), medic (*Medicago*), ryegrass (*Lolium*) or fescue (*Festuca*) species, or functionally active fragments or variants thereof.

The present invention further provides substantially purified or isolated nucleic acids or nucleic acid fragments complementary or antisense to the nucleic acids or nucleic acid fragments encoding PAP1 transcription factors or functionally active fragments or variants thereof.

The present invention also provides substantially purified or isolated nucleic acids or nucleic acid fragments encoding amino acid sequences for a class of proteins which are related to PAP1, or functionally active fragments or variants thereof. Such proteins are referred to herein as PAP1-like.

By a PAP1-like polypeptide is meant that either one of both of the following criteria apply: (i) the gene which encodes the polypeptide is expressed in a similar manner to PAP1, and (ii) the polypeptide has similar functional activity to PAP1. In a preferred embodiment, the PAP1-like polypeptide has at least approximately 70%, preferably at least approximately 80%, more preferably at least approximately 90% identity to PAP1.

Also provided are substantially purified or isolated nucleic acids or nucleic acid fragments complementary and antisense to PAP1-like encoding nucleic acid fragments.

Applicant has found that the individual or simultaneous enhancement or otherwise manipulation of the expression of PAP1 or PAP1-like polypeptides in plants may enhance or otherwise alter flavonoid biosynthesis; may enhance or otherwise alter the plant capacity for protein binding, metal chelation, anti-oxidation, or UV-light absorption; may enhance or reduce or otherwise alter plant pigment production.

Applicant has also found that the individual or simultaneous enhancement or otherwise manipulation of the expression of ANR or ANR-like polypeptides in plants may enhance or otherwise alter flavonoid biosynthesis; may enhance or otherwise alter the plant capacity for protein binding, metal chelation, anti-oxidation, or UV-light absorption; may enhance or reduce or otherwise alter plant pigment production.

In a particularly preferred embodiment applicant has found that the sequential, simultaneous or combined over-expression of candidates for PAP1 and ANR (*BANYULS*) from plant species, including clover (*Trifolium*), medic (*Medicago*), ryegrass (*Lolium*) and fescue (*Festuca*) species, may confer enhanced herbage quality and/or bloat-safety on plants, such as pasture plants, preferably through up-regulation of condensed tannins in for example their leaves.

Methods for the manipulation of PAP1 and/or ANR or -like gene activities in plants, including legumes such as clovers (*Trifolium* species), lucerne (*Medicago sativa*) and grass species such as ryegrasses (*Lolium* species) and fescues (*Festuca* species), may facilitate the production of, for example, forage legumes and forage grasses and other crops with enhanced tolerance to biotic stresses such as viruses, microorganisms, insects and fungal pathogens; altered pigmentation in flowers; forage legumes with enhanced herbage quality and bloat-safety; crops with enhanced isoflavonoid content leading to health benefits.

The use of transcription factors to modify multiple product-specific enzymes in the flavonoid pathway may be a useful alternative strategy to cloning genes encoding many enzymes and modifying their expression in transgenic plants.

The clover (*Trifolium*), medic (*Medicago*), ryegrass (*Lolium*) or fescue (*Festuca*) species may be of any suitable type, including white clover (*Trifolium repens*), red clover (*Trifolium pratense*), subterranean clover (*Trifolium subterraneum*), alfalfa (*Medicago sativa*), Italian or annual ryegrass (*Lolium multiflorum*), perennial ryegrass (*Lolium perenne*), tall fescue (*Festuca arundinacea/Lolium arundinaceum*), meadow fescue (*Festuca pratensis*) and red fescue (*Festuca rubra*). Preferably the species is a clover or a ryegrass, more preferably white clover (*T. repens*) or perennial ryegrass (*L. perenne*). White clover (*Trifolium repens* L.) and perennial ryegrass (*Lolium perenne* L.) are key pasture legumes and grasses, respectively, in temperate climates throughout the world. Perennial ryegrass is also an important turf grass.

Nucleic acids according to the invention may be full-length genes or part thereof, and are also referred to as "nucleic acid fragments" and "nucleotide sequences" in this specification. For convenience, the expression "nucleic acid or nucleic acid fragment" is used to cover all of these.

The nucleic acid or nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

Such nucleic acids or nucleic acid fragments could be assembled to form a consensus contig. As used herein, the term "consensus contig" refers to a nucleotide sequence that is assembled from two or more constituent nucleotide sequences that share common or overlapping regions of sequence homology. For example, the nucleotide sequence of two or more nucleic acids or nucleic acid fragments can be compared and aligned in order to identify common or overlapping sequences. Where common or overlapping sequences exist between two or more nucleic acids or nucleic acid fragments, the sequences (and thus their corresponding nucleic acids or nucleic acid fragments) can be assembled into a single contiguous nucleotide sequence.

In a preferred embodiment of this aspect of the invention, the substantially purified or isolated nucleic acid or nucleic acid fragment encoding a PAP1 or PAP 1-like protein, or complementary or antisense to a sequence encoding a PAP 1 or PAP 1-like protein, includes a nucleotide sequence selected from the group consisting of (a) the sequences shown in FIGS. 1 and 4A and 4B hereto (Seq ID Nos: 1 and 3, respectively); (b) the complements of the sequences recited in (a); (c) the sequences antisense to the sequences recited in (a) and (b); and (d) functionally active fragments and variants of the sequences recited in (a), (b) and (c).

By "functionally active" in relation to nucleic acids it is meant that the fragment or variant (such as an analogue, derivative or mutant) encodes a polypeptide, which is capable of modifying flavonoid biosynthesis; in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 75% identity to the relevant part of the above mentioned nucleotide sequence, more preferably at least approximately 80% identity, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 30 nucleotides, more preferably at least 45 nucleotides, most preferably at least 60 nucleotides.

Nucleic acids or nucleic acid fragments encoding at least a portion of a candidate PAP1 ortholog have been isolated and identified. The nucleic acids or nucleic acid fragments of the present invention may be used to isolate cDNAs and genes encoding homologous proteins from the same or other plant species. Isolation of homologous genes using sequence-dependent protocols, such as methods of nucleic acid hybridisation, and methods of DNA and RNA amplification as exemplified by various uses of nucleic acid amplification technologies (e.g. polymerase chain reaction, ligase chain reaction), is well known in the art.

For example, genes encoding other PAP1-like proteins, either as cDNAs or genomic DNAs, may be isolated directly by using all or a portion of the nucleic acids or nucleic acid fragments of the present invention as hybridisation probes to screen libraries from the desired plant employing the methodology well known to those skilled in the art. Specific oligonucleotide probes based upon the nucleic acid sequences of the present invention may be designed and synthesized by methods known in the art. Moreover, the entire sequences may be used directly to synthesize DNA probes by methods known to the skilled artisan such as random primer DNA labelling, nick translation, or end-labelling techniques, or RNA probes using available in vitro transcription systems. In addition, specific primers may be designed and used to amplify a part or all of the sequences of the present invention. The resulting amplification products may be labelled directly during amplification reactions or labelled after amplification reactions, and used as probes to isolate full-length cDNA or genomic fragments under conditions of appropriate stringency.

In addition, short segments of the nucleic acids or nucleic acid fragments of the present invention may be used in protocols to amplify longer nucleic acids or nucleic acid fragments encoding homologous genes from DNA or RNA. For example, polymerase chain reaction may be performed on a library of cloned nucleic acid fragments wherein the sequence of one primer is derived from the nucleic acid sequences of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol (Frohman et al. (1988) *Proc. Natl. Acad. Sci. USA* 85:8998, the entire disclosure of which is incorporated herein by reference) to generate cDNAs by using PCR to amplify copies of the region between a single point in the transcript and the 3' or 5' end. Using commercially available 3' RACE and 5' RACE systems (BRL), specific 3' or 5' cDNA fragments may be isolated (Ohara et al. (1989) *Proc. Natl. Acad Sci USA* 86:5673; Loh et al. (1989) *Science* 243:217, the entire disclosures of which are incorporated herein by reference). Products generated by the 3' and 5' RACE procedures may be combined to generate full-length cDNAs.

In a second aspect of the present invention there is provided a substantially purified or isolated flavonoid biosynthesis-regulating transcription factor from a legume or grass species. Preferably, the present invention provides a substantially purified or isolated polypeptide selected from the group consisting of PAP1 and PAP1-like proteins, and functionally active fragments and variants thereof, preferably from a clover (*Trifolium*), medic (*Medicago*), ryegrass (*Lolium*) or fescue (*Festuca*) species.

The clover (*Trifolium*), medic (*Medicago*), ryegrass (*Lolium*) or fescue (*Festuca*) species may be of any suitable type, including white clover (*Trifolium repens*), red clover (*Trifolium pratense*), subterranean clover (*Trifolium subterraneum*), alfalfa (*Medicago sativa*), Italian or annual ryegrass (*Lolium multiflorum*), perennial ryegrass (*Lolium perenne*), tall fescue (*Festuca arundinacea/Lolium arundinaceum*), meadow fescue (*Festuca pratensis*) and red fescue (*Festuca rubra*). In particular, the species may be a clover or a ryegrass, more particularly white clover (*T. repens*) or perennial ryegrass (*L. perenne*).

In a preferred embodiment of this aspect of the invention, the substantially purified or isolated PAP1 or PAP1-like polypeptide includes an amino acid sequence selected from the group consisting of the sequences shown in FIGS. 2 and 5 hereto (SEQ ID Nos: 2 and 4, respectively), and functionally active fragments and variants thereof.

By "functionally active" in relation to polypeptides it is meant that the fragment or variant has one or more of the biological properties of the proteins PAP1 and PAP1-like, respectively. Additions, deletions, substitutions and derivatizations of one or more of the amino acids are contemplated so long as the modifications do not result in loss of functional activity of the fragment or variant. Preferably the functionally active fragment or variant has at least approximately 60% identity to the relevant part of the above mentioned amino acid sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

In a further embodiment of this aspect of the invention, there is provided a polypeptide recombinantly produced from a nucleic acid or nucleic acid fragment according to the present invention.

Availability of the nucleotide sequences of the present invention and deduced amino acid sequences facilitates immunological screening of cDNA expression libraries. Synthetic peptides representing portions of the instant amino acid sequences may be synthesized. These peptides may be used to immunise animals to produce polyclonal or monoclonal antibodies with specificity for peptides and/or proteins including the amino acid sequences. These antibodies may be then used to screen cDNA expression libraries to isolate full-length cDNA clones of interest.

In a still further aspect of the present invention there is provided a method of isolating a nucleic acid or nucleic acid fragment of the present invention said method including sequencing nucleic acid fragments from a nucleic acid library.

The nucleic acid library may be of any suitable type and is preferably a cDNA library.

The nucleic acid or nucleic acid fragment may be isolated from a recombinant plasmid or may be amplified, for example using polymerase chain reaction.

The sequencing may be performed by techniques known to those skilled in the art.

In a still further aspect of the present invention there is provided use of a nucleic acid or nucleic acid fragment of the present invention, and/or nucleotide sequence information thereof, as a molecular genetic marker.

More particularly, nucleic acids or nucleic acid fragments according to the present invention and/or nucleotide sequence information thereof may be used as a molecular genetic marker for quantitative trait loci (QTL) tagging, QTL mapping, DNA fingerprinting and in marker assisted selection, particularly in clovers, alfalfa, ryegrasses and fescues. Even more particularly, nucleic acids or nucleic acid fragments according to the present invention and/or nucleotide sequence information thereof may be used as molecular genetic markers in plant improvement in relation to plant tolerance to biotic stresses such as viruses, microorganisms, insects, fungal pathogens; in relation to forage quality; in relation to bloat safety; in relation to condensed tannin content; in relation to plant pigmentation. Even more particularly, sequence information revealing SNPs in allelic variants of the nucleic acids or nucleic acid fragments of the present invention and/or nucleotide sequence information thereof may be used as molecular genetic markers for QTL tagging and mapping and in marker assisted selection, particularly in clovers, alfalfa, ryegrasses and fescues.

In a still further aspect of the present invention there is provided a construct including a nucleic acid or nucleic acid fragment according to the present invention.

The term "construct" as used herein refers to an artificially assembled or isolated nucleic acid molecule, which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

In a still further aspect of the present invention there is provided a vector including a nucleic acid or nucleic acid fragment according to the present invention.

In a still further aspect of the present invention there is provided a construct or vector including a nucleic acid or nucleic acid fragment encoding a PAP1 or PAP1-like transcription factor, or a functionally active fragment or variant thereof. Optionally, the construct or vector may further include a nucleic acid or nucleic acid fragment encoding ANR (*BANYULS*), or a functionally active fragment or variant thereof. Preferably the nucleic acids or nucleic acid fragments encode PAP1 or ANR from a legume or grass species, such as a clover (*Trifolium*), medic (*Medicago*), ryegrass (*Lolium*) and/or fescue (*Festuca*) species.

The term "vector" as used herein encompasses both cloning and expression vectors. Vectors are often recombinant molecules containing nucleic acid molecules from several sources.

In a preferred embodiment of this aspect of the invention, the vector may include a regulatory element such as a promoter, a nucleic acid or nucleic acid fragment according to the present invention and a terminator; said regulatory element, nucleic acid or nucleic acid fragment and terminator being operatively linked.

By "operatively linked" is meant that said regulatory element is capable of causing expression of said nucleic acid or nucleic acid fragment in a plant cell and said terminator is capable of terminating expression of said nucleic acid or nucleic acid fragment in a plant cell. Preferably, said regulatory element is upstream of said nucleic acid or nucleic acid fragment and said terminator is downstream of said nucleic acid or nucleic acid fragment.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, integrative or viable in the plant cell.

The regulatory element and terminator may be of any suitable type and may be endogenous to the target plant cell or may be exogenous, provided that they are functional in the target plant cell.

Preferably the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (eg. monocotyledon or dicotyledon). Particularly suitable constitutive promoters include the Cauliflower Mosaic Virus 35S (CaMV 35S) promoter, the maize Ubiquitin promoter, and the rice Actin promoter.

A variety of terminators which may be employed in the vectors of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the regulatory element, the nucleic acid or nucleic acid fragment of the present invention and the terminator, may include further elements necessary for expression of the nucleic acid or nucleic acid fragment, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene], and reporter genes (such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, northern and western blot hybridisation analyses.

Those skilled in the art will appreciate that the various components of the vector are operatively linked, so as to result in expression of said nucleic acid or nucleic acid fragment. Techniques for operatively linking the components of the vector of the present invention are well known to those skilled in the art. Such techniques include the use of linkers, such as synthetic linkers, for example including one or more restriction enzyme sites.

The vectors of the present invention may be incorporated into a variety of plants, including monocotyledons (such as grasses from the genera *Lolium, Festuca, Paspalum, Pennisetum, Panicum* and other forage and turfgrasses, corn, oat, sugarcane, wheat and barley), dicotyledons (such as *arabidopsis*, tobacco, clovers, medics, eucalyptus, potato, sugarbeet, canola, soybean, chickpea) and gymnosperms. In a preferred embodiment, the vectors may be used to transform monocotyledons, preferably grass species such as ryegrasses (*Lolium* species) and fescues (*Festuca* species), more preferably perennial ryegrass, including forage- and turf-type cultivars. In an alternate preferred embodiment, the vectors may be used to transform dicotyledons, preferably forage legume species such as clovers (*Trifolium* species) and medics (*Medicago* species), more preferably white clover (*Trifolium repens*), red clover (*Trifolium pratense*), subterranean clover (*Trifolium subterraneum*) and alfalfa (*Medicago sativa*). Clovers, alfalfa and medics are key pasture legumes in temperate climates throughout the world.

Techniques for incorporating the vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a vector or construct, nucleic acid or nucleic acid fragment of the present invention.

The plant cell, plant, plant seed or other plant part may be from any suitable species, including monocotyledons, dicotyledons and gymnosperms. In a preferred embodiment the plant cell, plant, plant seed or other plant part may be from a monocotyledon, preferably a grass species, more preferably a ryegrass (*Lolium* species) or fescue (*Festuca* species), more preferably perennial ryegrass, including both forage- and turf-type cultivars. In an alternate preferred embodiment the plant cell, plant, plant seed or other plant part may be from a dicotyledon, preferably forage legume species such as clovers (*Trifolium* species) and medics (*Medicago* species), more preferably white clover (*Trifolium repens*), red clover (*Trifolium pratense*), subterranean clover (*Trifolium subterraneum*) and alfalfa (*Medicago sativa*).

The present invention also provides a plant, plant seed or other plant part, or a plant extract derived from a plant cell of the present invention, and preferably including e.g. transformed with, a vector or construct, nucleic acid or nucleic acid fragment of the present invention.

Using the methods and materials of the present invention, flavonoid biosynthesis may be increased or decreased. It may be increased, for example by incorporating additional copies of a sense nucleic acid of the present invention. It may be decreased, for example, by incorporating an antisense nucleic acid or dsRNA or small interfering RNA (siRNA) derived from the nucleotide sequences of the present invention. In addition, the number of copies of genes encoding different enzymes involved in flavonoid biosynthesis may be manipulated to modify flavonoid biosynthesis, protein binding, metal chelation, anti oxidation, UV light absorption, plant pigment production, plant defense to biotic stresses and modifying forage quality.

In a further aspect of the present invention there is provided a method of modifying flavonoid biosynthesis; of modifying protein binding, metal chelation, anti-oxidation, and UV-light absorption; of modifying plant pigment production; of modifying plant defense to biotic stresses such as viruses, microorganisms, insects, fungal pathogens; of modifying forage quality by disrupting protein foam and conferring protection from rumen pasture bloat, said method including introducing into said plant an effective amount of a nucleic acid or nucleic acid fragment, construct and/or vector according to the present invention.

The present invention also provides a method of enhancing herbage quality and/or bloat safety in a plant, which method includes over-expressing PAP1 and ANR (*BANYULS*) in said plant in a sequential, simultaneous or combined manner.

In a preferred embodiment, the method includes introducing into said plant an effective amount of one or more nucleic acids or nucleic acid fragments encoding PAP1 and ANR (*BANYULS*), preferably from a legume or grass species, such as clover (*Trifolium*), medic (*Medicago*), ryegrass (*Lolium*) and/or fescue (*Festuca*) species.

In a further preferred embodiment, the plant is a pasture plant.

By "an effective amount" it is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

Using the methods and materials of the present invention, flavonoid biosynthesis, protein binding, metal chelation, anti-oxidation, UV-light absorption, tolerance to biotic stresses such as viruses, microorganisms, insects and fungal pathogens; pigmentation in for example flowers and leaves; herbage quality and bloat-safety; isoflavonoid content leading to health benefits, may be increased or otherwise altered, for example by incorporating additional copies of a sense nucleic acid or nucleic acid fragment of the present invention. They may be decreased or otherwise altered, for example by incorporating an antisense nucleic acid or nucleic acid fragment of the present invention.

The present invention will now be more fully described with reference to the accompanying Examples and drawings. It should be understood, however, that the description following is illustrative only and should not be taken in any way as a restriction on the generality of the invention described above.

In the Figures

FIG. 1 shows the nucleotide sequence of TrPAP1 expressed sequence tag (SEQ ID No: 1).

FIG. 2 shows the deduced amino acid sequence of TrPAP1 expressed sequence tag (SEQ ID No: 2).

FIGS. 4A and 4B show the nucleotide sequence of the white clover PAP1 full-length cDNA (SEQ ID No: 3).

FIG. 5 shows the deduced amino acid sequence of the white clover PAP1 full length cDNA (SEQ ID No: 4).

FIG. 6 shows plasmid maps of the cDNA encoding white clover PAP1 in the sense and antisense orientations in a modified pPZP221 binary transformation vector.

Figure 9:
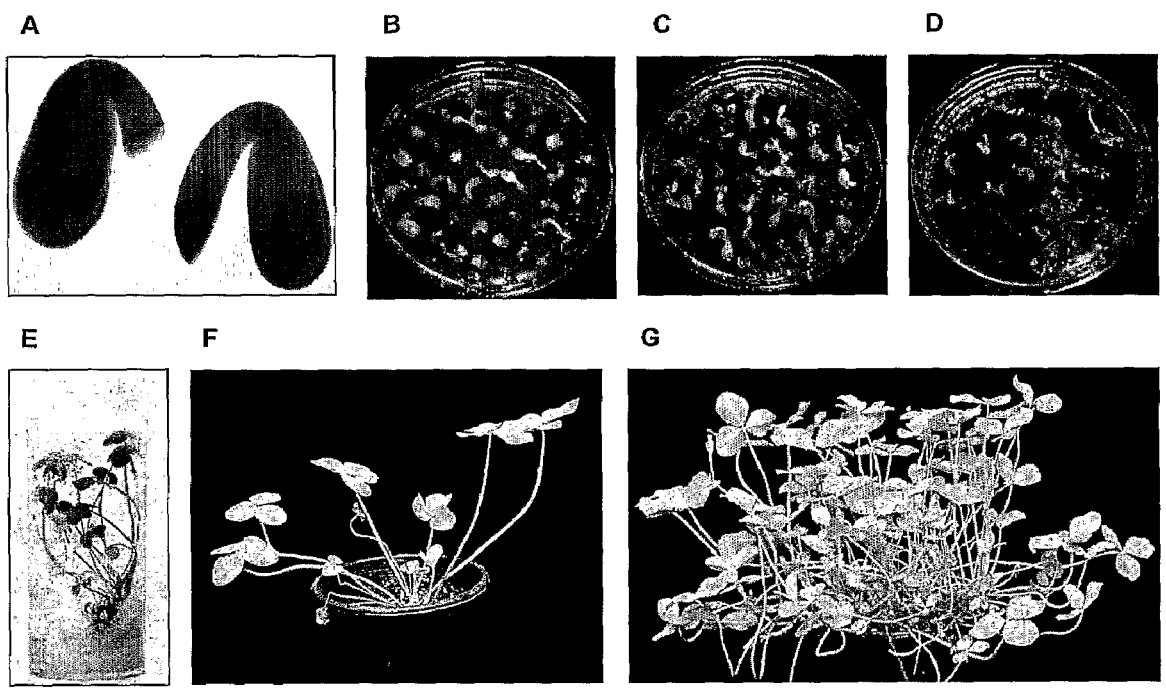

FIG. 9 shows steps of selection during *Agrobacterium*-mediated transformation of white clover cotyledons. Cotyledonary explants are extracted from imbibed seeds (A), co-cultivated with *Agrobacterium tumefaciens* strain containing the binary transformation vector and subjected to a series of 2-week selective steps on tissue culture plates (B, C and D). Shoots are excised and grown on root-inducing media in tissue culture vessels (E). Finally, transgenic white clover plantlets are transferred to glasshouse conditions (F and G), allowing molecular and phenotypic analyses to take place.

Figure 10:
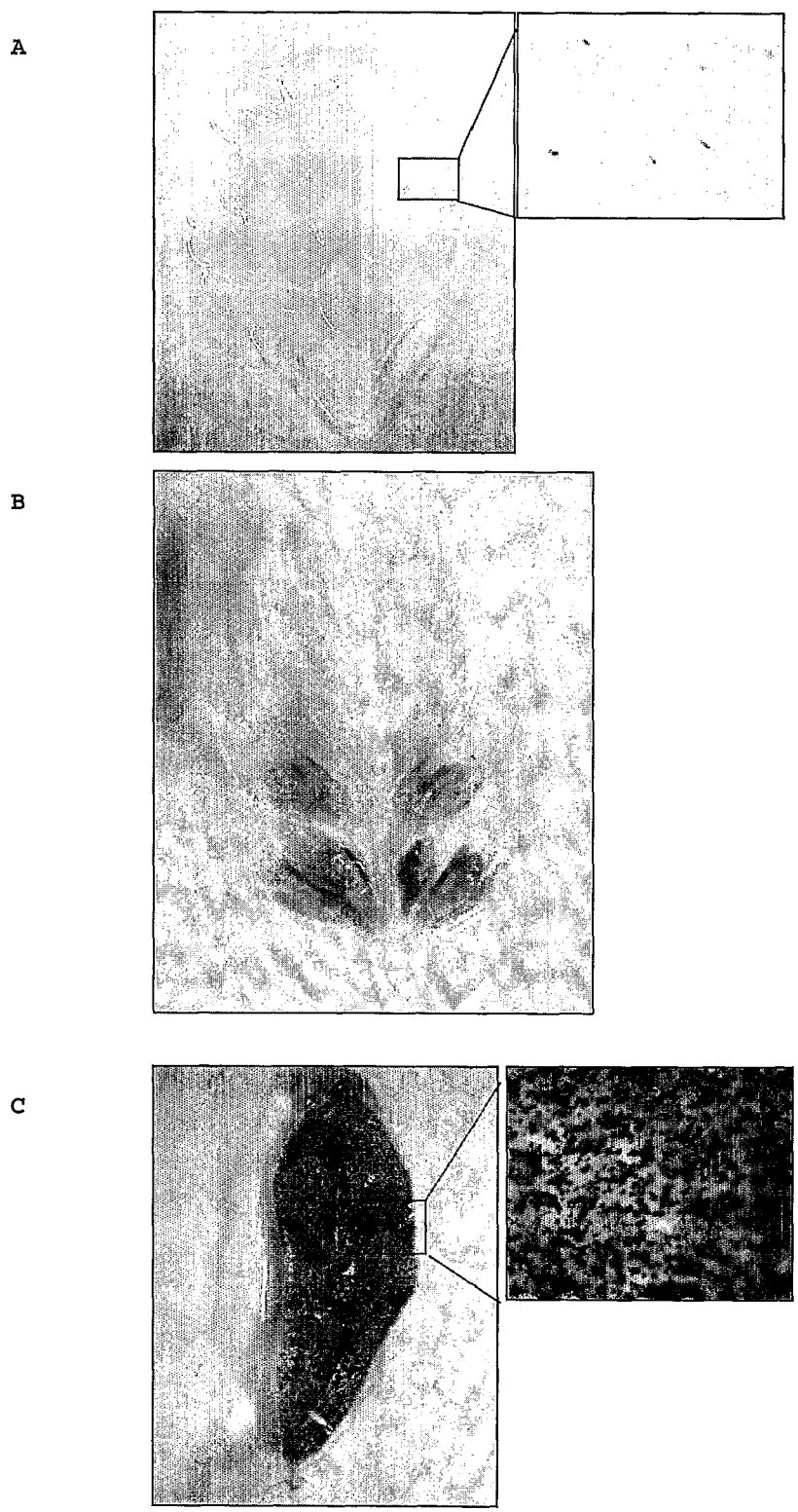

FIG. 10 shows 4-dimethylaminocinnemaldehyde (DMACA) staining patterns in *Trifolium repens* (cv 'Mink') leaf (A) and immature inflorescence (B) tissue and in *Lotus corniculatus* (cv 'Draco') leaf tissue (C).

Figure 11:
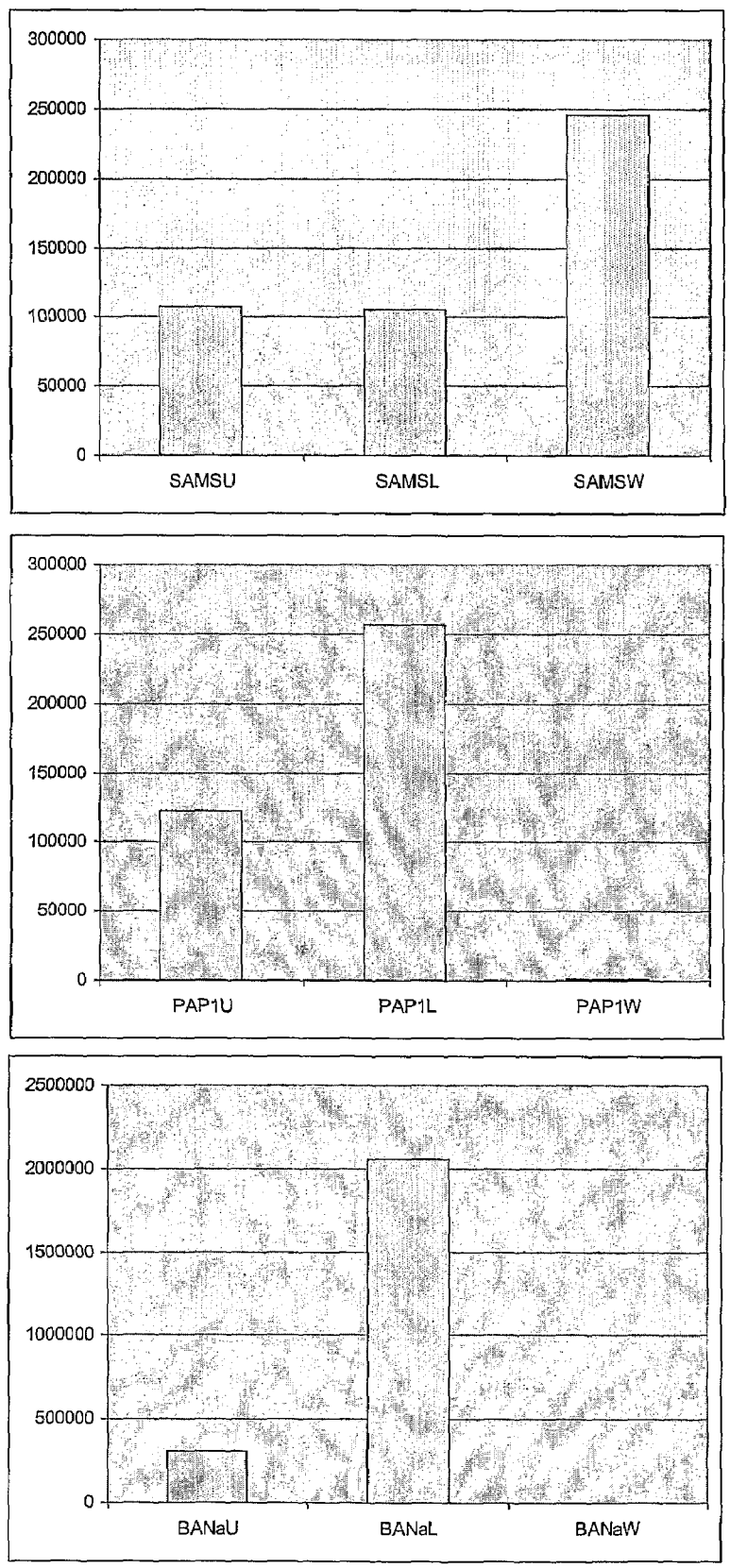

FIG. 11 shows comparative expression of the clover homologues of the flavonoid-related genes BANYULS (anthocyanidin reductase) and PAP1 and the ubiquitously-expressed s-adenosyl-methionine synthetase (SAMS) gene, normalised against expression of elongation factor 1 alpha (EF-1α), another ubiquitously-expressed gene. Gene expression was measured by real-time RT-PCR with SYBR Green chemistry in upper (U), lower (L) and whole (W) immature buds of *T. repens* cv Mink. Primer sets were designed using cDNA clones of flavonoid-related genes (Table 4) and the δδCT method of data analysis.

EXAMPLE 1

Preparation of cDNA Libraries, Isolation and Sequencing of the cDNA Coding for PAP1-Like Proteins from White Clover (*Trifolium repens*)

cDNA libraries representing mRNAs from various organs and tissues of white clover (*Trifolium repens*) were prepared. The characteristics of the white clover libraries, respectively, are described below (Tables 1 and 2).

TABLE 1 cDNA libraries from white clover (*Trifolium repens*)

| Library | Organ/Tissue |
|---|---|
| 01wc | Whole seedling, light grown |
| 02wc | Nodulated root 3, 5, 10, 14, 21 & 28 day old seedling |
| 03wc | Nodules pinched off roots of 42 day old rhizobium inoculated plants |
| 04wc | Cut leaf and stem collected after 0, 1, 4, 6 & 14 h after cutting |
| 05wc | Inflorescences: <50% open, not fully open and fully open |
| 06wc | Dark grown etiolated |
| 07wc | Inflorescence - very early stages, stem elongation, <15 petals, 15-20 petals |
| 08wc | seed frozen at −80° C., imbibed in dark overnight at 10° C. |
| 09wc | Drought stressed plants |
| 10wc | AMV infected leaf |
| 11wc | WCMV infected leaf |
| 12wc | Phophorus starved plants |
| 13wc | Vegetative stolon tip |
| 14wc | stolon root initials |
| 15wc | Senescing stolon |
| 16wc | Senescing leaf |

The cDNA libraries may be prepared by any of many methods available. For example, total RNA may be isolated using the Trizol method (Gibco-BRL, USA) or the RNeasy Plant Mini kit (Qiagen, Germany), following the manufacturers' instructions. cDNAs may be generated using the SMART PCR cDNA synthesis kit (Clontech, USA), cDNAs may be amplified by long distance polymerase chain reaction using the Advantage 2 PCR Enzyme system (Clontech, USA), cDNAs may be cleaned using the GeneClean spin column (Bio 101, USA), tailed and size fractionated, according to the protocol provided by Clontech. The cDNAs may be introduced into the pGEM-T Easy Vector system 1 (Promega, USA) according to the protocol provided by Promega. The cDNAs in the pGEM-T Easy plasmid vector are transfected into *Escherichia coli* Epicurian coli XL10-Gold ultra competent cells (Stratagene, USA) according to the protocol provided by Stratagene.

Alternatively, the cDNAs may be introduced into plasmid vectors for first preparing the cDNA libraries in Uni-ZAP XR vectors according to the manufacturer's protocol (Stratagene Cloning Systems, La Jolla, Calif., USA). The Uni-ZAP XR libraries are converted into plasmid libraries according to the protocol provided by Stratagene. Upon conversion, cDNA inserts will be contained in the plasmid vector pBluescript. In addition, the cDNAs may be introduced directly into precut pBluescript II SK(+) vectors (Stratagene) using T4 DNA ligase (New England Biolabs), followed by transfection into *E. coli* DH10B cells according to the manufacturer's protocol (GIBCO BRL Products).

Once the cDNA inserts are in plasmid vectors, plasmid DNAs are prepared from randomly picked bacterial colonies containing recombinant plasmids, or the insert cDNA sequences are amplified via polymerase chain reaction using primers specific for vector sequences flanking the inserted cDNA sequences. Plasmid DNA preparation may be performed robotically using the Qiagen QiaPrep Turbo kit (Qiagen, Germany) according to the protocol provided by Qiagen. Amplified insert DNAs are sequenced in dye-terminator sequencing reactions to generate partial cDNA sequences (expressed sequence tags or "ESTs"). The resulting ESTs are analyzed using an Applied Biosystems ABI 3700 sequence analyser.

EXAMPLE 2

DNA Sequence Analysis

The cDNA clone encoding a PAP1-like protein was identified by conducting BLAST (Basic Local Alignment Search Tool; Altschul et al. (1993) *J. Mol. Biol.* 215:403-410) searches. The cDNA sequence obtained was analysed for similarity to all publicly available DNA sequences contained in the eBioinformatics nucleotide database using the BLASTN algorithm provided by the National Center for Biotechnology Information (NCBI). The DNA sequence was translated in all reading frames and compared for similarity to all publicly available protein sequences contained in the SWISS-PROT protein sequence database using BLASTX algorithm (v 2.0.1) (Gish and States (1993) *Nature Genetics* 3:266-272) provided by the NCBI.

EXAMPLE 3

Identification and Full-length Sequencing of the cDNA Encoding the White Clover PAP1 Protein To fully characterise for the purposes of the generation of probes for hybridisation experiments and the generation of transformation vectors, the cDNA encoding the white clover PAP1 protein was identified and fully sequenced.

The full-length cDNA was identified from our EST sequence database using relevant published sequences (NCBI databank) as queries for BLAST searches. The full-length cDNA was identified by alignment of the query and hit sequences using Sequencher (Gene Codes Corp., Ann Arbor, M148108, USA). The original cDNA in the pGEM-T easy vector was then used to transform chemically competent DH5 alpha cells (Invitrogen, Carlsbad, USA). At least two colonies per transformation were picked for initial sequencing with M13F and M13R primers. The resulting sequences were aligned with the original EST sequence using Sequencher to confirm identity and one of the two clones was picked for full-length sequencing, usually the one with the best initial sequencing result.

Sequencing was completed by primer walking, i.e. an oligonucleotide primer was designed to the initial sequence and used for further sequencing from the 5' end. The sequence of this oligonucleotide primer is shown in Table 2. An extended poly-A tail necessitated the sequencing of the cDNA to be completed from the 5' end.

The contig was then assembled in Sequencher. The contig included the 5' end of the original EST sequence and extended beyond the poly-A tail at the 3' end of the cDNA.

Figure 3:
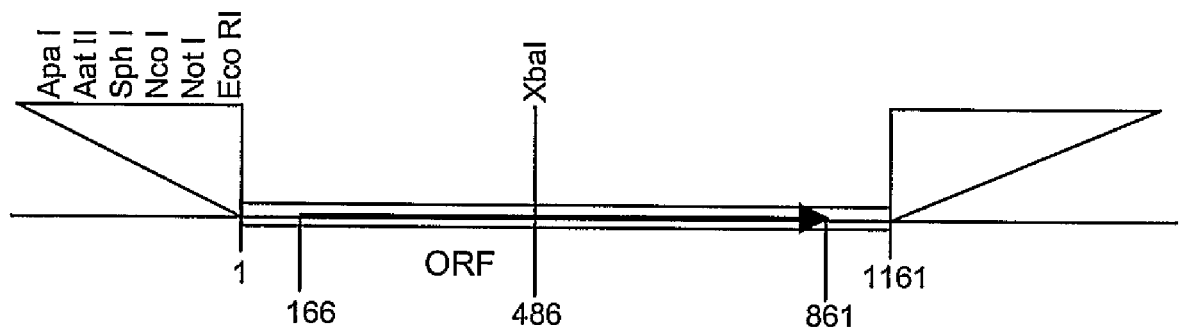
FIG. 3 shows a plasmid map of the full-length cDNA encoding white clover PAP1

The plasmid map and the full cDNA sequences of the white clover PAP1 gene in the pGEM-T Easy vector were obtained (FIGS. 3 and 4A and 4B).

TABLE 2

Primer used for sequencing of the full-length cDNA

| gene name | clone ID | sequencing primer | primer sequence (5' > 3') |
|---|---|---|---|
| TrPAP1 | 05wc1SsA01 | 05wc1SsA01.f1 | CAGGAAGGACAGCAAATGA (SEQ ID No. 5) |

EXAMPLE 4

Development of Binary Transformation Vectors Containing Chimeric Genes with cDNA Sequences from White Clover TrBANa and TrPAP1

Figure 8:
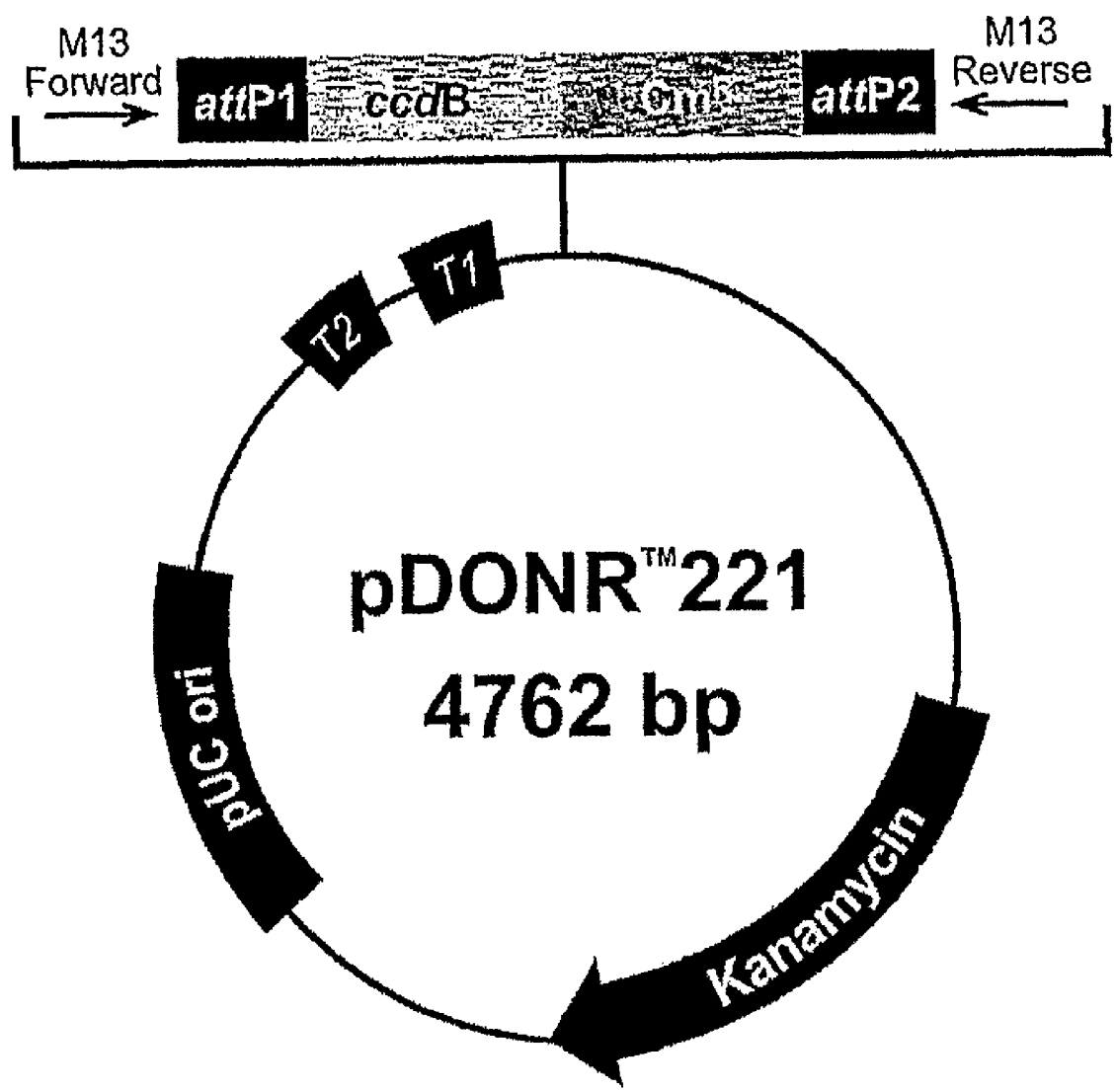
FIG. 8 shows a plasmid map of the pDONR221 GATE-WAY entry vector (Invitrogen, Carlsbad, USA).

To alter the expression of the proteins involved in flavonoid biosynthesis, protein binding, metal chelation, anti-oxidation, UV-light absorption, tolerance to biotic stresses such as viruses, micro-organisms, insects and fungal pathogens; pigmentation in for example flowers and leaves; herbage quality and bloat-safety and isoflavonoid content leading to health benefits by using antisense and/or sense suppression technology and over-expression of clover TrPAP1 and TrBANa homologues in transgenic plants, a set of sense and antisense binary transformation vectors was produced.

cDNA fragments were generated by high fidelity PCR using the original pGEM-T Easy plasmid cDNA as a template. The primers used (Table 3) contained attB1 and attB2 GATEWAY® recombination sites for directional cloning into the target vector. After PCR amplification and purification of the products, the cDNA fragments were cloned into the recombination site of the pDONR221™ vector (FIG. 8) using BP GATEWAY® technology (Invitrogen, Carlsbad, USA). The pPZPRCS2 binary vector (Hajdukiewicz et al., 1994) was modified to contain the 35S² cassette from pKYLX71: 35S² as follows. pKYLX71:35S² was cut with ClaI. The 5' overhang was filled in using Klenow and the blunt end was A-tailed with Taq polymerase. After cutting with EcoRI, the 2 kb fragment with an EcoRI-compatible and a 3'-A tail was gel-purified. pPZP221 was cut with HindIII and the resulting 5' overhang filled in and T-tailed with Taq polymerase. The remainder of the original pPZP221 multi-cloning site was removed by digestion with EcoRI, and the expression cassette cloned into the EcoRI site and the 3' T overhang restoring the HindIII site. This binary vector contains between the left and right border the plant selectable marker gene aaaC1 under the control of the 35S promoter and 35S terminator and the pKYLX71:35S²-derived expression cassette with a CaMV 35S promoter with a duplicated enhancer region and an rbcS terminator. This vector was GATEWAY®-enabled by digesting it with XbaI and blunt-ending using Klenow DNA polymerase, allowing the RfA recombination cassette to be cloned in the sense or antisense orientation between the enhanced 35S promoter and the rbcS terminator.

Transformation vectors containing chimeric genes using full-length open reading frame cDNAs encoding the white clover TrPAP1 protein in the sense orientation and antisense orientations under the control of the CaMV 35S or 35S² promoters were generated using GATEWAY® technology (FIG. 6). The orientation of the white clover PAP1 constructs (sense or antisense) was checked by restriction enzyme digestion and sequencing.

Figure 7:
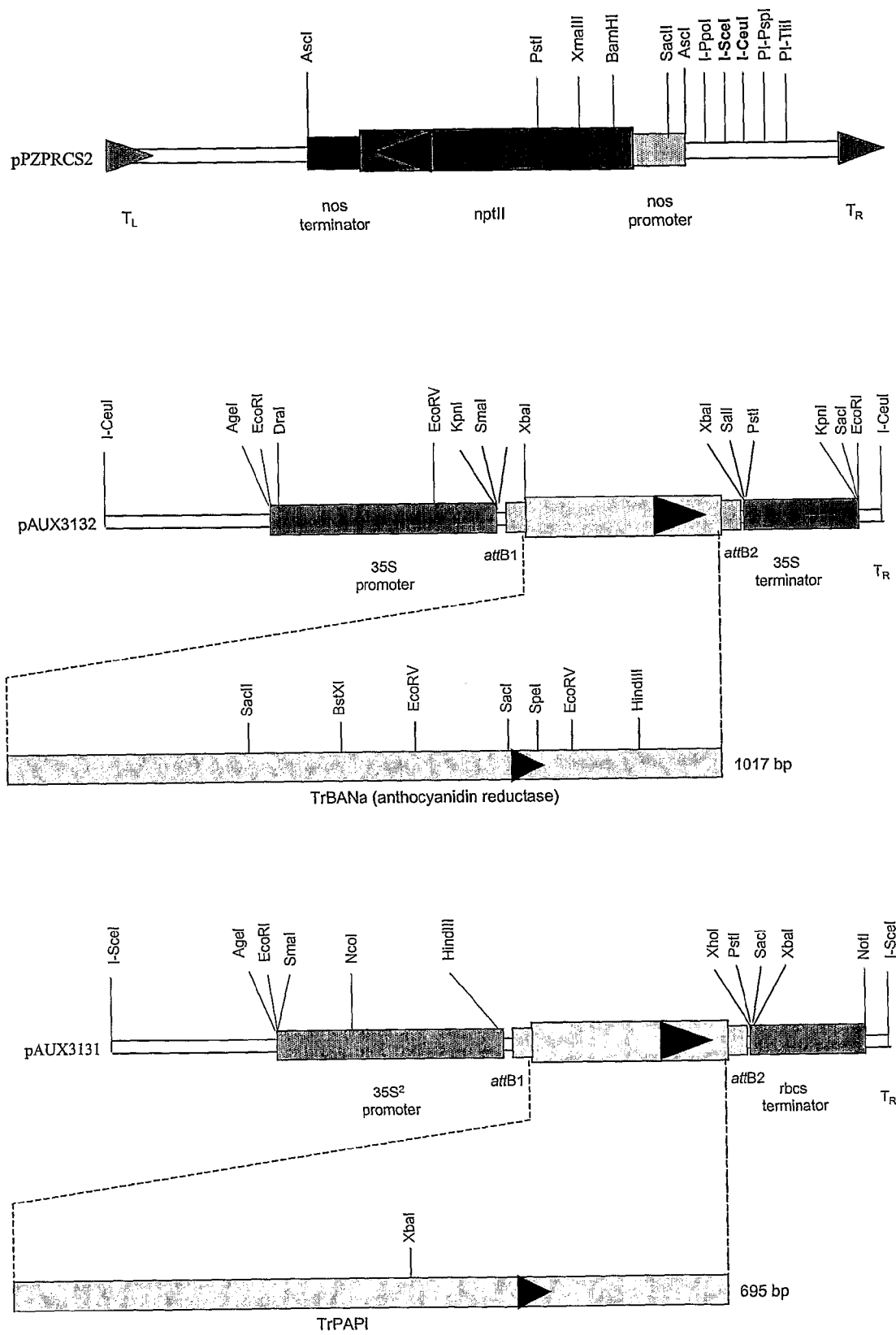
FIG. 7 shows plasmid maps of the pPZPRCS2 binary transformation vector containing the nptII selectable marker gene and of the pAUX3132 and pAUX3131 auxiliary vectors containing cDNAs encoding white clover anthocyanidin reductase (TrBANa) and PAP1 in the sense of orientation.

A multigene transformation vector based on the system of Goderis et al. (2002) was developed in order to modify the expression of white clover homologues of ANR and PAP1 in transgenic plants. The enhanced 35S promoter linked to the rbcS terminator was amplified by high-fidelity PCR from a pPZP200-based vector (Hajdukiewicz et al., 1994) using oligonucleotide primers designed to add an AgeI site to the 5' end and a NotI site to the 3' end of the PCR fragment (Table 3). This pPZP200-based vector had been modified as already described to contain the 35S2:rbcs expression cassette and a nos promoter:nptII:nos terminator selectable marker cassette. The PCR product and pAUX3131 were digested with AgeI and NotI and ligated together. A cassette containing the 35S promoter linked to the 35S terminator was cut from the pDH51 vector using EcoRI and cloned into the EcoRI site of pAUX3132. The modified versions of pAUX3131 and pAUX3132 were GATEWAY®-enabled by digesting them with BamHI and blunt-ending using Klenow DNA polymerase, allowing the RfB recombination cassette to be cloned in the sense orientation between the promoter and terminator sequences of each vector. Auxiliary vectors containing chimeric genes using full-length open reading frame cDNAs encoding the white clover BAN and PAP1 genes in the sense orientation under the control of the CaMV 35S or 35S² promoters were generated using GATEWAY® technology (FIG. 7).

A nos promoter:nptII:nos terminator selectable marker cassette encoding kanamycin resistance was amplified by high-fidelity PCR from the modified pPZP200 vector already described, using primers designed to add AscI sites to the 5' and 3' ends (Table 3). The PCR product and the pPZPRCS2 binary transformation vector (Goderis et al., 2002) were digested using AscI and ligated together (FIG. 7). The white clover BAN and PAP1 cassettes were added to this binary transformation vector by sequential digestions and ligations involving the homing enzymes I-CeuI and I-SceI, respectively (FIG. 7)

TABLE 3

List of primers used to PCR-amplify the open reading frames of flavonoid-related genes from white clover and expression cassettes used in binary transformation vectors

| gene name | clone ID | primer | primer sequence (5'->3') |
|---|---|---|---|
| TrBANa | 05wc2XsG02 | TrBANaGW.f | GGGGACAAGTTTGTACAAA AAAGCAGGCTTCTAGAGCA CTAGTGTGTATAAGTTTCT TGG (SEQ ID No: 6) |
| TrBANa | 05wc2XsG02 | TrBANaGW.r | GGGGACCACTTTGTACAAG AAAGCTGGGTCTAGATCAA AATCTAATTCTTCAGTGC (SEQ ID No: 7) |
| TrPAP1 | 05wc1SsA01 | TrPAP1GW.f | GGGGACAAGTTTGTACAAA AAGCAGGCTTCATGGGTGG TGTTGCATGGAC (SEQ ID No: 8) |

TABLE 3-continued

List of primers used to PCR-amplify the open reading frames of flavonoid-related genes from white clover and expression cassettes used in binary transformation vectors

| gene name | clone ID | primer | primer sequence (5'->3') |
|---|---|---|---|
| TrPAP1 | 05wc1SsA01 | TrPAP1GW.r | GGGGACCACTTTGTACAAG AAAGCTGGGTCCTAAGAAG AAAAATCATTATACATATC (SEQ ID No: 9) |
| 35S2: rbcs cassette | N/A | P35S2AgeI.f | ATAATAACCGGTGCCCGGG GATCTCCTTTGCC (SEQ ID No: 10) |
| 35S2: rbcs cassette | N/A | TrbcsNotI.r | ATAATAGCGGCCGCATGCA TGTTGTCAATCAATTGG (SEQ ID No: 11) |
| Nos: nptII: nos cassette | N/A | PnosAscI.f | ATAATAGGCGCGCCTGATC ATGAGCGGAGAATTAAGGG (SEQ ID No: 12) |
| Nos: nptII: nos cassette | N/A | TnosAscI.r | ATAATAGGCGCGCCTAGTA ACATAGATGACACCGCG (SEQ ID No: 13) |

EXAMPLE 5

Production and Analysis of Transgenic White Clover Plants Carrying Chimeric White Clover TrBANa and TrPAP1 Genes Involved in Flavonoid Biosynthesis A set of transgenic white clover plants carrying white clover genes involved in flavonoid biosynthesis, protein binding, metal chelation, anti-oxidation, UV-light absorption, tolerance to biotic stresses such as viruses, micro-organisms, insects and fungal pathogens; pigmentation in for example flowers and leaves; herbage quality and bloat-safety and isoflavonoid content leading to health benefits, were produced.

pPZP221-based transformation vectors with TrBANa and TrPAP1 cDNAs comprising the full open reading frame sequences in sense and antisense orientations under the control of the CaMV 35S promoter with duplicated enhancer region ($35S^2$) were generated as detailed in Example 4.

Agrobacterium-mediated gene transfer experiments were performed using these transformation vectors.

The production of transgenic white clover plants carrying the white clover TrBANa and TrPAP1 cDNAs under the control of the CaMV 35S promoter with and without the duplicated enhancer region ($35S^2$) is described here in detail. The selection process is shown in FIG. 9.

Preparation of White Clover Cotyledonary Explants

White clover (cv 'Mink') seeds were rinsed for 5 minutes in running tap water and incubated twice, for 5 minutes in 70% v/v ethanol in a 120 ml tissue culture container with gentle shaking. The same container was used to incubate the seeds for 2 minutes in 1% sodium hypochlorite (1:3 ratio of Domestos™ bleach in water) with gentle shaking. The seeds were then rinsed six times in sterile water in a laminar flow hood and incubated for 18 hours at 4° C. in the dark. Cotyledonary explant were extracted using 10 ml syringes attached to 21 G needles (Terumo, Japan) under a dissecting microscope in a laminar flow hood. Both layers of the seed coat were peeled away, the end of the hypocotyl was cut off and the cotyledons with approximately 4 mm of hypocotyl were separated and transferred to a 90×90×20 mm petri dish containing MGL medium.

Preparation of Agrobacterium

Agrobacterium tumefaciens strain AGL-1 containing each PZP221-derived binary expression vector was streaked on LB medium containing 50 μg/ml rifampicin and 100 μg/ml spectinomycin and grown at 27° C. for 48 hours. A single colony was used to inoculate 5 ml of LB medium containing 50 μg/ml rifampicin and 100 μg/ml spectinomycin and grown over night at 27° C. and 250 rpm on an orbital shaker. The overnight culture was used as an inoculum for 40 ml of YEP medium containing 100 μg/ml spectinomycin and 40 mg/l acetosyringone. Incubation was over night at 27° C. and 250 rpm on an orbital shaker in a 250 ml Erlenmeyer flask.

The overnight cultures were centrifuged for 15 min at 5500×g and the supernatant discarded. The cells were resuspended in MGL media with 40 mg/l acetosyringone to a volume corresponding to an $OD_{600}$ reading of 0.4. The cells were then incubated at 27° C. and 250 rpm until the $OD_{600}$ reading reached 0.8.

Cocultivation and Selection of White Clover Transformants

The MGL medium was removed from the petri dish containing white clover cotyledonary explants and replaced with the prepared Agrobacterium suspension using a sterile serological pipette. The petri dish was sealed with laboratory film, covered with aluminium foil and incubated with gentle shaking for 45 min. The dish was opened in the laminar flow hood and the Agrobacterium suspension removed with a pipette. The explants were then transferred to plates containing RM73 media with 40 mg/l acetosyringone (Table 4) and incubated for 3 days in a plant tissue culture room at 22° C. with a 16 hour photoperiod. After this, the explants were transferred, with the hypocotyl end in the media, to plates containing RM73 media with 75 mg/l gentamicin and 250 mg/l cefotaxime. The explants were transferred to fresh plates every two weeks for 6-8 weeks. Shoots were then transferred to 120 ml tissue culture vessels containing RIM media (Table 5) with 75 mg/l gentamicin and 250 mg/l cefotaxime. When roots had developed, the plantlets were transferred to pots of soil and after 2 weeks of recovery in a misting bench, were grown under standard glasshouse conditions.

Preparation of Genomic DNA 1-2 leaflets of white clover plants recovered from the transformation process were harvested and freeze-dried. The tissue was homogenised on a Retsch MM300 mixer mill, then centrifuged for 10 min at 1700×g to collect cell debris. Genomic DNA was isolated from the supernatant using Wizard Magnetic 96 DNA Plant System kits (Promega) on a Biomek FX (Beckman Coulter). 5 μl of the sample (50 μl) were then analysed on an agarose gel to check the yield and the quality of the genomic DNA.

Analysis of DNA from Putative Transgenic Lines Using Real-time PCR

Genomic DNA was analysed for the presence of the transgene by real-time PCR using SYBR Green chemistry. PCR primer pairs were designed to detect the aacC1 gentamycin resistance gene and the nptII kanamycin resistance gene in the transferred T-DNA regions of pPZP221 and pPZPRCS2-based binary transformation vectors, respectively, using MacVector (Accelrys). The sequences of these primers are as follows:

```
nptII.f
5'-GGCTATGACTGGGCACAACA-3'      (SEQ ID No: 14)

nptII.r
5'-ACCGGACAGGTCGGTCTTG-3'       (SEQ ID No: 15)

pPZPaacC1-1.r.f
5'-TCAAGTATGGGCATCATTCGCAC-3'   (SEQ ID No: 16)

pPZPaacC1-1.r
5'-TGCTCAAACCGGGCAGAACG-3'      (SEQ ID No: 17)
```

1 µl of each genomic DNA sample was run in a 25 µl PCR reaction including SYBR Green on an ABI (Applied Biosystems) together with samples containing DNA isolated from wild type white clover plants (cv 'Mink', negative control), samples containing buffer instead of DNA (buffer control) and samples containing the plasmid used for transformation (positive plasmid control).

TABLE 4

Composition of RM73 tissue culture media, pH 5.75

| Component | [Stock] | For 1 litre |
|---|---|---|
| MS Macronutients | 10 x | 100 mL |
| MS Micronutrients | 100 x | 10 mL |
| MS Vitamins | 100 x | 10 mL |
| TDZ | 100 mM | 50 uL |
| NAA | 1 mM | 0.5 mL |
| Sucrose (BDH Chemicals) | — | 30 g |
| Agar | — | 8 g |

TABLE 5

Composition of root-inducing tissue culture media (RIM73), pH 5.75

| Component | [Stock] | For 1 litre |
|---|---|---|
| MS macronutrients | 10 x | 100 mL |
| MS micronutrients | 100 x | 10 mL |
| MS vitamins | 100 x | 10 mL |
| Indole-3-butyric acid | 1 mM | 1.2 mL |
| Sucrose (BDH Chemicals) | — | 15 g |
| Agar (Becton-Dickinson) | — | 8 g |

EXAMPLE 6

Analysis of Condensed Tannins and their Monomers in the Leaves of Transgenic White Clover Plants Carrying Chimeric White Clover TrPAP1 and TrBANa Genes Involved in Flavonoid Biosynthesis Accumulation of condensed tannins and their monomers was analysed qualitatively in leaves of transgenic and wild type (cv 'Mink') white clover plants using 4-dimethylaminocinnemaldehyde (DMACA) staining. Two mature leaflets from each plant were decolourised in absolute ethanol in 6-well tissue culture plates for 3 hours with gentle shaking. The ethanol was removed and replaced with a 0.01% w/v solution of DMACA (Fluka), freshly made up in absolute ethanol with 2.4% v/v concentrated hydrochloric acid. After 1 hour of incubation with gentle shaking, the leaflets were rinsed with distilled water and mounted in 50% glycerol for analysis with a dissecting microscope. Wild type white clover plants show blue staining in epidermal cells in the floral organs and in trichomes. Lotus corniculatus (cv 'Draco'), a forage legume with a 'bloat-safe' level of condensed tannins in the leaves, shows blue staining of approximately 50% of mesophyll cells in leaves (FIG. 10). Achieving a level of condensed tannins in white clover leaves that is comparable to the level seen in leaves of L. corniculatus by metabolic engineering would be agronomically valuable.

DMACA staining can detect economically significant levels of condensed tannins and their monomers in the leaves of established bloat-safe forage legumes. However, the condensation of catechin monomers to form condensed tannins and their transport from the cytoplasm to the vacuole is poorly understood. Hence, modifying the regulation of known enzymes and transcription factors in the flavonoid pathway may up-regulate catechin levels but not increase condensed tannin levels, and therefore, bloat-safety. The PVPP-butanol-HCl assay detects only condensed tannins, relying on the ability of condensed tannins, but not their monomers to bind to PVPP. The detailed method is as follows.

Clover leaf and inflorescence (positive control) tissue was snap-frozen and ground to a fine powder in a mortar and pestle under liquid nitrogen. After grinding, 0.75 g of the powder from each sample was transferred to a 14 ml screw-cap centrifuge tube (Falcon), vortex-mixed with 1.5 ml of extraction buffer containing 80% v/v methanol in distilled water with 5.3 mM sodium bisulfite. Samples were mixed for 5 hours on a mixing wheel before centrifugation at 3000×g for 10 minutes. A 1 ml aliquot of each supernatant was transferred to a 1.5 ml microcentrifuge tube and reduced to 0.25 ml in a vacuum centrifuge. Equal volumes of the sample were added to each of two 1.5 ml microcentrifuge tubes containing 25 mg of polyvinyl polypyrrolidone (PVPP). Each mixture was vortex-mixed intermittently for 15 min and centrifuged for 1 min at maximum speed in a microcentrifuge. After removal of the supernatant, the pellet was washed four times with 1 ml of methanol, with a 1 min centrifugation step at maximum speed in a microcentrifuge between each wash. A freshly-made 70:30 (v/v) solution of butanol and concentrated hydrochloric acid was added to each pellet and one tube of the mixture was incubated for 1 hour at 70° C., whereas the other tube was incubated at ambient temperature. The difference in the absorbance (530 nm) between the two tubes from each plant sample was proportional to the level of condensed tannins in the sample. This assay can be quantitated with a condensed tannin of known concentration, although only the relative levels of tannins were measured in this experiment.

EXAMPLE 7

Design of Real Time RT-PCR Primers Based on the cDNA Sequences of the Clover TrPAP1 Gene Real-time RT-PCR is a recently developed technique that allows more quantitative analyses of gene expression than Northern or conventional RT-PCR experiments. Essentially, real-time RT-PCR with SYBR Green chemistry and gene-specific primers involves the automatic measurement of the level of a fluorescent PCR product generated from a cDNA species over each cycle. The abundance of each template is proportional to the amplification rate. Therefore, a threshold corresponding to the start of the exponential phase of PCR allows the relative abundance of target genes to be standardised against a uniformly expressed 'housekeeping' gene in each tissue and compared to a negative control without a template. Real-time RT-PCR with SYBR Green chemistry has been used successfully by others in the field to quantify the expression of four flavonoid-related genes in Lotus corniculatus plants exposed to different light regimes (Paolocci et al., 2005)

A Real-Time RT-PCR strategy involving SYBR Green chemistry and the δδCT method of analysis was used to characterise the expression of TrPAP1 and TrBANa, in white clover tissues containing high and low levels of condensed tannins, relative to expression of the ubiquitously-expressed genes, elongation factor-1α (SAMS) and S-adenosyl methionine synthase (SAMS). This approach aimed to determine whether TrPAP1 and TrBANa are involved in condensed tannin production, or in the production of other flavonoids, and could therefore be targeted for overexpression or downregulation in the metabolic engineering of bloat-safe white clover.

The full-length cDNA sequences of white clover TrPAP1, TrBANa, SAMS and EF-1α homologues were used as input data for the Primer Express (Applied Biosystems, Foster City, USA) primer design program, using the default settings, no 3' GC clamp and a predicted amplicon size of 50-150 base pairs. Primers close to the 3' ends of the input sequences were preferred, due to the likelihood of a large number of cDNA molecules derived from clover samples being incomplete at the 5' end. The sequences of the chosen primers are shown in Table 6.

The specificity of the primer sets was confirmed using 1 ul of plasmid DNA (0.01 ng/ul) from the original cDNA cloned into pGEM-T Easy or autoclaved, purified water, 12.5 ul 2×SYBR Green Master Mix (Applied Biosystems), 0.5 ul each of the forward and reverse primers (10 uM) and 10.5 ul of autoclaved, purified water (Sartorius A G, Goettingen, Germany). Real-time PCR was performed in 96-well optical PCR plates (Applied Biosystems) using the Stratagene MX3000P cycler and the following cycling parameters: 95° C. for 10 min, 40 cycles of 95° C. for 30 sec and 60° C. for 1 min, followed by 55° C. for 1 min and 95° C. for 1 min with a cycle threshold cut-off of 24 cycles It was shown by DMACA staining that buds in the lower half of immature Mink white clover inflorescences are enriched for condensed tannins (FIG. 10). Therefore the expression of the clover PAP1 and BAN genes in the buds of white clover (cv Mink), relative to expression of a clover histone control gene was tested. Total RNA was extracted from upper and lower halves of immature inflorescences as well as whole immature inflorescences using the RNeasy kit (QIAGEN GmbH, Hilden, Germany) and contaminating genomic DNA was digested on the column using the optional on-column DNAse digestion according to the manufacturers' instructions. Complementary DNA (cDNA) was synthesised from 0.5 ug of total RNA using the Quantitect Reverse Transcriptase Kit (QIAGEN GmbH). Real-time RT-PCR reactions were set up and run as described earlier using 1 ul of cDNA, plasmid control DNA or autoclaved, purified water as the template. The expression of clover BAN and PAP1 homologues correlated well with condensed tannin production in mature buds within the lower half of immature white clover inflorescences (FIG. 11).

TABLE 6

List of primers designed for Real-time RT-PCR analysis of condensed tannin-rich organs of white clover, based on the cDNA sequences of white clover genes

| Gene name | Clone ID | primer 1 (forward) | primer 2 (reverse) |
|---|---|---|---|
| TrEF-1α | 14wc2PsG04 | TCGAGAAGGAAGCTGCTGAAA (SEQ ID No: 18) | CCCAGGCATACTTGAATGACCT (SEQ ID No: 19) |
| TrSAMS | 05wc3HsD02 | AGAGGAGGTTGGTGCTGGTG (SEQ ID No: 20) | TCAGTGGCATAGCCAAACATGT (SEQ ID No: 21) |
| TrBANa | 05wc2XsG02 | TTGCTACACCTGTGAACTTTGCTT (SEQ ID No: 22) | GCAATTGCTTTCAACACATTCAAC (SEQ ID No: 23) |
| TrPAP1 | 05wc1SsA01 | ATCGAGTTCCTCTGTTGGCAG (SEQ ID No: 24) | GCCTACAACTCTTTCGGCATCT (SEQ ID No: 25) |

REFERENCES

Frohman et al. (1988) Rapid production of full-length cDNAs from rare transcripts: amplification using a single gene-specific oligonucleotide primer. *Proc. Natl. Acad. Sci. USA* 85:8998

Gish and States (1993) Identification of protein coding regions by database similarity search. *Nature Genetics* 3:266-272

Goderis, I. J. W. M., De Bolle, M. F. C., Francois, I. E. J. A., Wouters, P. F. J., Broekaert, W. F. and Cammue, B. P. A. (2002). A set of modular plant transformation vectors allowing flexible insertion of up to six expression units. *Plant Mol. Biol.* 50:17-27.

Hajdukiewicz, P., Svab, Z., Maliga, P. (1994). The small versatile pPZP family of *Agrobacterium* binary vectors for plant transformation. *Plant Mol. Biol.* 25:989-994.

Loh, E. Y., Elliott, J. F., Cwirla, S., Lanier, L. L., Davis, M. M. (1989). Polymerase chain reaction with single-sided specificity: Analysis of T-cell receptor delta chain. *Science* 243: 217-220

Ohara, O., Dorit, R. L., Gilbert, W. (1989). One-sided polymerase chain reaction: The amplification of cDNA. *Proc. Natl. Acad Sci USA* 86:5673-5677

Paolocci, F., Bovone, T. Tosti, N., Arcioni, S, and Damiani, F. (2005). Light and an exogenous transcription factor qualitatively and quantitatively affect the biosynthetic pathway of condensed tannins in *Lotus corniculatus* leaves. *J. Exp. Bot.* 56: 1093-1103

Finally, it is to be understood that various alterations, modifications and/or additions may be made without departing from the spirit of the present invention as outlined herein.

It will also be understood that the term "comprises" (or its grammatical variants) as used in this specification is equivalent to the term "includes" and should not be taken as excluding the presence of other elements or features.

Documents cited in this specification are for reference purposes only and their inclusion is not acknowledgment that they form part of the common general knowledge in the relevant art.

The invention claimed is:

1. A substantially purified or isolated nucleic acid or nucleic acid fragment encoding a PURPLE ANTHOCYANIN PIGMENT 1(PAP 1) or a PAP 1-like protein, or complementary or antisense to a sequence encoding a PAP 1 or PAP 1-like protein, selected from the group consisting of (a) Sequence ID Nos: 1 and 3; (b) complements of the sequences recited in (a); (c) sequences antisense to the sequences recited in (a) and (b); (d) functionally active fragments of the sequences recited in (a), (b) and (c) having a size of at least 60 nucleotides; and (e) functionally active variants of the sequences recited in (a), (b) and (c) having at least 90% identity with the sequences recited in (a), (b) or (c).

2. A vector comprising the nucleic acid or nucleic acid fragment according to claim 1.

3. A vector according to claim 2, further comprising a promoter and a terminator, said promoter, nucleic acid or nucleic acid fragment and terminator being operatively linked.

4. The vector according to claim 2, further comprising a nucleic acid or nucleic acid fragment encoding anthocyanidin reductase (ANR) or a functionally active fragment or variant thereof.

5. The vector according to claim 4 wherein the nucleic acids or nucleic acid fragment encoding ANR or a functionally active fragment or variant thereof is from a species selected from the group consisting of clover (*Trifolium*), medic (*Medicago*), ryegrass (*Lolium*) and fescue (*Festuca*).

6. A plant cell, plant, plant seed or other plant part, comprising the vector according to claim 2.

7. A plant, plant seed or other plant part derived from the plant cell or plant according to claim 6.

8. The nucleic acid according to claim 1 wherein said functionally active variants have at least 95% identity with the sequences recited in (a), (b) or (c).

9. The nucleic acid according to claim 1 wherein said nucleic acid or nucleic acid fragment is selected from the group consisting of Sequence ID Nos: 1 and 3.

10. A substantially purified or isolated PAP1 or PAP1-like polypeptide comprising an amino acid sequence selected from the group consisting of Sequence ID Nos: 2 and 4; and functionally active variants having at least 90% identity with SEQ ID No: 2 or 4.

11. The polypeptide according to claim 10 comprising an amino acid sequence selected from the group consisting of Sequence ID Nos: 2 and 4.

12. A substantially purified or isolated nucleic acid or nucleic acid fragment encoding the polypeptide according to claim 10.

* * * * *

SEQUENCE LISTING

<160> NUMBER OF SEQ ID NOS: 25

<210> SEQ ID NO 1
<211> LENGTH: 583
<212> TYPE: DNA
<213> ORGANISM: Trifolium repens

<400> SEQUENCE: 1
ataacacaat attatatata aaagaagatg ctggtgatgg cttgattatt atgagtgtga      60
aaagtggtgg tgtttgtaga gtctcataag atgggtggtg ttgcatggac agaagaagaa     120
gatcatttgc ttaagaaatg catacaacaa tatggtgaag gaaagtggca tcgagttcct     180
ctgttggcag gtctaaacag atgccgaaag agttgtaggc taagatggtt gaactatctc     240
cgtcctaaca tcaagagagg aaattttgct gaggaggaag ttgaaatgat tgtcaaacta     300
cacaaattat taggcaacag atggtcccta attgcaggaa ggctaccagg aaggacagca     360
aatgatgtga aaaactattg gaattgtcat ctaagcaaaa gagtaaatgc tctagaagct     420
gaccaagatg gatcacaatt atccaaagat gttcaaatca ttatgccaca gccaagaaac     480
aatggttcaa gctcaacaat gaagagaagg agccaaggag actcaccaac taatcaagtt     540
ctagttgaac aagagagtga catgacaaaa tttgatgctg atg                       583

<210> SEQ ID NO 2
<211> LENGTH: 164
<212> TYPE: PRT
<213> ORGANISM: Trifolium repens

<400> SEQUENCE: 2

Met Gly Gly Val Ala Trp Thr Glu Glu Asp His Leu Leu Lys Lys
1               5                   10                  15

Cys Ile Gln Gln Tyr Gly Glu Gly Lys Trp His Arg Val Pro Leu Leu
                20                  25                  30

Ala Gly Leu Asn Arg Cys Arg Lys Ser Cys Arg Leu Arg Trp Leu Asn
            35                  40                  45

Tyr Leu Arg Pro Asn Ile Lys Arg Gly Asn Phe Ala Glu Glu Val
    50                  55                  60

Glu Met Ile Val Lys Leu His Lys Leu Leu Gly Asn Arg Trp Ser Leu
65                  70                  75                  80

Ile Ala Gly Arg Leu Pro Gly Arg Thr Ala Asn Asp Val Lys Asn Tyr
                85                  90                  95

Trp Asn Cys His Leu Ser Lys Arg Val Asn Ala Leu Glu Ala Asp Gln
                100                 105                 110

Asp Gly Ser Gln Leu Ser Lys Asp Val Gln Ile Ile Met Pro Gln Pro
            115                 120                 125

Arg Asn Asn Gly Ser Ser Ser Thr Met Lys Arg Arg Ser Gln Gly Asp
    130                 135                 140

Ser Pro Thr Asn Gln Val Leu Val Glu Gln Glu Ser Asp Met Thr Lys
145                 150                 155                 160

Phe Asp Ala Asp

<210> SEQ ID NO 3
<211> LENGTH: 1161
<212> TYPE: DNA
<213> ORGANISM: Trifolium repens

<400> SEQUENCE: 3

```
aattcgatta agcagtggta acaacgcaga gtacgcgggg acatcttcaa gaaacatgtg    60
tgtgtgtcaa ttcacataac acaatattat atataaagaa gatgctggt gatggcttga   120 ttattatgag tgtgaaaagt ggtggtgttt gtagagtctc ataagatggg tggtgttgca   180
tggacagaag aagaagatca tttgcttaag aaatgcatac aacaatatgg tgaaggaaag   240
tggcatcgag ttcctctgtt ggcaggtcta acagatgcc gaaagagttg taggctaaga   300
tggttgaact atctccgtcc taacatcaag agaggaaatt ttgctgagga ggaagttgaa   360
atgattgtca aactacacaa attattaggc aacagatggt ccctaattgc aggaaggcta   420
ccaggaagga cagcaaatga tgtgaaaaac tattggaatt gtcatctaag caaaagagta   480
aatgctctag aagctgacca agatggatca caattatcca aagatgttca atcattatg   540 ccacagccaa gaacaatgg ttcaagctca acaatgaaga gaaggagcca aggagactca   600
ccaactaatc aagttctagt tgaacaagag agtgacatga caaaatttga tgctgatgga   660
aagaacaata tgattgaatc acaacaagac atgatgatg attcatgctt agatcaacaa   720
ggtatgttta gtgagtttcc aatggacttt caattagaag gatttgaagc tatggtaagt   780
ggaggagaag gtagtagtag ccaatggaat tgggatgatt tgctcttaga tatggatatg   840
tataatgatt tttcttctta gattatcatc ccttgttatg tttctaatag ggaagacaat   900
ggtagtcttt ataccttggt tgtgtattaa tatcaaagtt aaatgttttc caaggaaatg   960
catggtaact aaattggtca tgtattttgt aaattgaagt cattgctaat aaaattaacc  1020
aataaagtcg gtcttgtaag gccgagttag tccaaaaaaa aaaaaaaaaa aaaaaaaaa   1080 aaaaaaaaaa aaaaaaaaaa ataaaaaaaa aaaaaaaaaa aaaaaaaaaa agtactctgc  1140
gttgttacca ctgcttaatc a                                            1161

<210> SEQ ID NO 4
<211> LENGTH: 231
<212> TYPE: PRT
<213> ORGANISM: Trifolium repens

<400> SEQUENCE: 4

Met Gly Gly Val Ala Trp Thr Glu Glu Asp His Leu Leu Lys Lys
1               5                  10                  15

Cys Ile Gln Gln Tyr Gly Glu Gly Lys Trp His Arg Val Pro Leu Leu
                20                  25                  30

Ala Gly Leu Asn Arg Cys Arg Lys Ser Cys Arg Leu Arg Trp Leu Asn
            35                  40                  45

Tyr Leu Arg Pro Asn Ile Lys Arg Gly Asn Phe Ala Glu Glu Val
        50                  55                  60

Glu Met Ile Val Lys Leu His Lys Leu Leu Gly Asn Arg Trp Ser Leu
65                  70                  75                  80

Ile Ala Gly Arg Leu Pro Gly Arg Thr Ala Asn Asp Val Lys Asn Tyr
                85                  90                  95

Trp Asn Cys His Leu Ser Lys Arg Val Asn Ala Leu Glu Ala Asp Gln
                100                 105                 110

Asp Gly Ser Gln Leu Ser Lys Asp Val Gln Ile Ile Met Pro Gln Pro
            115                 120                 125

Arg Asn Asn Gly Ser Ser Thr Met Lys Arg Arg Ser Gln Gly Asp
        130                 135                 140

Ser Pro Thr Asn Gln Val Leu Val Glu Gln Glu Ser Asp Met Thr Lys
145                 150                 155                 160

Phe Asp Ala Asp Gly Lys Asn Asn Met Ile Glu Ser Gln Gln Asp Met
                165                 170                 175
```

```
Met Met Tyr Ser Cys Leu Asp Gln Gln Gly Met Phe Ser Glu Phe Pro
            180                 185                 190

Met Asp Phe Gln Leu Glu Gly Phe Glu Ala Met Val Ser Gly Gly Glu
            195                 200                 205

Gly Ser Ser Ser Gln Trp Asn Trp Asp Asp Leu Leu Leu Asp Met Asp
    210                 215                 220

Met Tyr Asn Asp Phe Ser Ser
225                 230
```

<210> SEQ ID NO 5
<211> LENGTH: 19
<212> TYPE: DNA
<213> ORGANISM: Artificial Sequence
<220> FEATURE:
<223> OTHER INFORMATION: primer sequence

<400> SEQUENCE: 5
caggaaggac agcaaatga                                              19

<210> SEQ ID NO 6
<211> LENGTH: 60
<212> TYPE: DNA
<213> ORGANISM: Artificial Sequence
<220> FEATURE:
<223> OTHER INFORMATION: Primer sequence

<400> SEQUENCE: 6
ggggacaagt ttgtacaaaa aagcaggctt ctagagcact agtgtgtata agtttcttgg    60

<210> SEQ ID NO 7
<211> LENGTH: 56
<212> TYPE: DNA
<213> ORGANISM: Artificial Sequence
<220> FEATURE:
<223> OTHER INFORMATION: Primer sequence

<400> SEQUENCE: 7
ggggaccact ttgtacaaga aagctgggtc tagatcaaaa tctaattctt cagtgc         56

<210> SEQ ID NO 8
<211> LENGTH: 51
<212> TYPE: DNA
<213> ORGANISM: Artificial Sequence
<220> FEATURE:
<223> OTHER INFORMATION: Primer sequence

<400> SEQUENCE: 8
ggggacaagt ttgtacaaaa aagcaggctt catgggtggt gttgcatgga c              51

<210> SEQ ID NO 9
<211> LENGTH: 57
<212> TYPE: DNA
<213> ORGANISM: Artificial Sequence
<220> FEATURE:
<223> OTHER INFORMATION: Primer sequence

<400> SEQUENCE: 9
ggggaccact ttgtacaaga aagctgggtc taagaagaa aaatcattat acatatc         57

<210> SEQ ID NO 10
<211> LENGTH: 32
<212> TYPE: DNA
<213> ORGANISM: Artificial Sequence
<220> FEATURE:
<223> OTHER INFORMATION: Primer sequence -continued

<210> SEQ ID NO 10

<400> SEQUENCE: 10
ataataaccg gtgcccgggg atctcctttg cc                                    32

<210> SEQ ID NO 11
<211> LENGTH: 36
<212> TYPE: DNA
<213> ORGANISM: Artificial Sequence
<220> FEATURE:
<223> OTHER INFORMATION: Primer sequence

<400> SEQUENCE: 11
ataatagcgg ccgcatgcat gttgtcaatc aattgg                                36

<210> SEQ ID NO 12
<211> LENGTH: 38
<212> TYPE: DNA
<213> ORGANISM: Artificial Sequence
<220> FEATURE:
<223> OTHER INFORMATION: Primer sequence

<400> SEQUENCE: 12
ataataggcg cgcctgatca tgagcggaga attaaggg                              38

<210> SEQ ID NO 13
<211> LENGTH: 36
<212> TYPE: DNA
<213> ORGANISM: Artificial Sequence
<220> FEATURE:
<223> OTHER INFORMATION: Primer sequence

<400> SEQUENCE: 13
ataataggcg cgcctagtaa catagatgac accgcg                                36

<210> SEQ ID NO 14
<211> LENGTH: 20
<212> TYPE: DNA
<213> ORGANISM: Artificial Sequence
<220> FEATURE:
<223> OTHER INFORMATION: Primer sequence

<400> SEQUENCE: 14
ggctatgact gggcacaaca                                                  20

<210> SEQ ID NO 15
<211> LENGTH: 19
<212> TYPE: DNA
<213> ORGANISM: Artificial Sequence
<220> FEATURE:
<223> OTHER INFORMATION: Primer sequence

<400> SEQUENCE: 15
accggacagg tcggtcttg                                                   19

<210> SEQ ID NO 16
<211> LENGTH: 23
<212> TYPE: DNA
<213> ORGANISM: Artificial Sequence
<220> FEATURE:
<223> OTHER INFORMATION: Primer sequence

<400> SEQUENCE: 16
tcaagtatgg gcatcattcg cac                                              23

<210> SEQ ID NO 17
<211> LENGTH: 20

```
<212> TYPE: DNA
<213> ORGANISM: Artificial Sequence
<220> FEATURE:
<223> OTHER INFORMATION: Primer sequence

<400> SEQUENCE: 17
tgctcaaacc gggcagaacg                                               20

<210> SEQ ID NO 18
<211> LENGTH: 21
<212> TYPE: DNA
<213> ORGANISM: Artificial Sequence
<220> FEATURE:
<223> OTHER INFORMATION: Primer sequence

<400> SEQUENCE: 18
tcgagaagga agctgctgaa a                                             21

<210> SEQ ID NO 19
<211> LENGTH: 22
<212> TYPE: DNA
<213> ORGANISM: Artificial Sequence
<220> FEATURE:
<223> OTHER INFORMATION: Primer sequence

<400> SEQUENCE: 19
cccaggcata cttgaatgac ct                                            22

<210> SEQ ID NO 20
<211> LENGTH: 20
<212> TYPE: DNA
<213> ORGANISM: Artificial Sequence
<220> FEATURE:
<223> OTHER INFORMATION: Primer sequence

<400> SEQUENCE: 20
agaggaggtt ggtgctggtg                                               20

<210> SEQ ID NO 21
<211> LENGTH: 22
<212> TYPE: DNA
<213> ORGANISM: Artificial Sequence
<220> FEATURE:
<223> OTHER INFORMATION: Primer sequence

<400> SEQUENCE: 21
tcagtggcat agccaaacat gt                                            22

<210> SEQ ID NO 22
<211> LENGTH: 24
<212> TYPE: DNA
<213> ORGANISM: Artificial Sequence
<220> FEATURE:
<223> OTHER INFORMATION: Primer sequence

<400> SEQUENCE: 22
ttgctacacc tgtgaacttt gctt                                          24

<210> SEQ ID NO 23
<211> LENGTH: 24
<212> TYPE: DNA
<213> ORGANISM: Artificial Sequence
<220> FEATURE:
<223> OTHER INFORMATION: Primer sequence

<400> SEQUENCE: 23
gcaattgctt tcaacacatt caac                                          24
```

```
<210> SEQ ID NO 24
<211> LENGTH: 21
<212> TYPE: DNA
<213> ORGANISM: Artificial Sequence
<220> FEATURE:
<223> OTHER INFORMATION: Primer sequence

<400> SEQUENCE: 24
atcgagttcc tctgttggca g                                              21

<210> SEQ ID NO 25
<211> LENGTH: 22
<212> TYPE: DNA
<213> ORGANISM: Artificial Sequence
<220> FEATURE:
<223> OTHER INFORMATION: Primer sequence

<400> SEQUENCE: 25
gcctacaact ctttcggcat ct                                             22
```